(12) United States Patent
Cheatham et al.

(10) Patent No.: US 10,154,897 B2
(45) Date of Patent: Dec. 18, 2018

(54) INTRAOCULAR LENS SYSTEMS AND RELATED METHODS

(71) Applicant: ELWHA LLC, Bellevue, WA (US)

(72) Inventors: Jesse R. Cheatham, Seattle, WA (US); Roderick A. Hyde, Redmond, WA (US); John Marshall, Farnborough (GB); Clarence T. Tegreene, Mercer Island, WA (US); Lowell L. Wood, Bellevue, WA (US); Roberto Zaldivar, Mendoza (AR); Roger Zaldivar, Mendoza (AR)

(73) Assignee: ELWHA LLC, Bellevue, WA (US)

( * ) Notice: Subject to any disclaimer, the term of this patent is extended or adjusted under 35 U.S.C. 154(b) by 0 days.

(21) Appl. No.: 14/807,756

(22) Filed: Jul. 23, 2015

(65) Prior Publication Data
US 2017/0020661 A1    Jan. 26, 2017

(51) Int. Cl.
*A61F 2/16* (2006.01)
*A61B 3/103* (2006.01)

(52) U.S. Cl.
CPC ............ *A61F 2/1627* (2013.01); *A61B 3/103* (2013.01); *A61F 2/16* (2013.01); *A61F 2/1648* (2013.01); *A61F 2/1659* (2013.01); *A61F 2250/0002* (2013.01)

(58) Field of Classification Search
CPC ........ A61F 2/16; A61F 2/1624; A61F 2/1627; A61F 2/1659
See application file for complete search history.

(56) References Cited

U.S. PATENT DOCUMENTS

| | | | |
|---|---|---|---|
| 5,066,301 A | 11/1991 | Wiley | |
| 5,108,429 A | 4/1992 | Wiley | |
| 5,171,266 A | 12/1992 | Wiley et al. | |
| 5,203,788 A | 4/1993 | Wiley | |
| 5,344,447 A * | 9/1994 | Swanson .................. | A61F 2/16 |
| | | | 351/159.11 |
| 6,857,741 B2 | 2/2005 | Blum et al. | |
| 6,871,951 B2 | 3/2005 | Blum et al. | |
| 7,023,594 B2 | 4/2006 | Blum et al. | |
| 7,396,126 B2 | 7/2008 | Blum et al. | |

(Continued)

FOREIGN PATENT DOCUMENTS

| WO | WO 2009/153764 A2 | 12/2009 |
|---|---|---|
| WO | WO 2014/194432 A1 | 12/2014 |

OTHER PUBLICATIONS

PCT International Search Report; International App. No. PCT/US2016/043062; dated Oct. 21, 2016; pp. 1-3.

(Continued)

*Primary Examiner* — Dinah Baria
(74) *Attorney, Agent, or Firm* — Dorsey & Whitney LLP

(57) ABSTRACT

Embodiments disclosed herein are directed to intraocular lens systems includes at least one intraocular lens device and methods of using the same. The at least one intraocular lens device includes one or more photodetectors and an intraocular lens exhibiting a modifiable focal length. The one or more photodetectors are configured to detect light that is used to determine a presence of the object or the apparent object distance. The focal length of the intraocular lens can be modified depending on the determined presence of the object or the apparent object distance.

11 Claims, 12 Drawing Sheets

(56) References Cited

U.S. PATENT DOCUMENTS

| | | |
|---|---|---|
| 7,475,984 B2 | 1/2009 | Blum et al. |
| 7,517,083 B2 | 4/2009 | Blum et al. |
| 7,832,864 B2 | 11/2010 | Barrett et al. |
| 8,446,341 B2 | 5/2013 | Amirparviz et al. |
| 8,587,734 B2 | 11/2013 | Li |
| 8,608,800 B2 | 12/2013 | Portney |
| 8,885,139 B2 | 11/2014 | Peyghambarian et al. |
| 9,877,824 B2 | 1/2018 | Hyde et al. |
| 2002/0140899 A1 | 10/2002 | Blum et al. |
| 2003/0210377 A1 | 11/2003 | Blum et al. |
| 2003/0231293 A1 | 12/2003 | Blum et al. |
| 2004/0027501 A1 | 2/2004 | Blum et al. |
| 2005/0140924 A1 | 6/2005 | Blum et al. |
| 2005/0270481 A1 | 12/2005 | Blum et al. |
| 2006/0098164 A1 | 5/2006 | Blum et al. |
| 2006/0164593 A1 | 7/2006 | Peyghambarian et al. |
| 2007/0121065 A1 | 5/2007 | Cox et al. |
| 2008/0106633 A1 | 5/2008 | Blum et al. |
| 2008/0208335 A1 | 8/2008 | Blum et al. |
| 2009/0009717 A1 | 1/2009 | Barrett et al. |
| 2009/0032679 A1* | 2/2009 | Holladay ............ A61F 2/1618 250/201.2 |
| 2009/0105817 A1 | 4/2009 | Bretthauer et al. |
| 2009/0195749 A1 | 8/2009 | Blum et al. |
| 2010/0001926 A1 | 1/2010 | Amirparviz et al. |
| 2010/0002190 A1 | 1/2010 | Clarke et al. |
| 2010/0324408 A1 | 12/2010 | Klink et al. |
| 2011/0025955 A1 | 2/2011 | Bos et al. |
| 2012/0140167 A1* | 6/2012 | Blum ................... A61F 2/1624 351/159.34 |
| 2013/0035760 A1 | 2/2013 | Portney |
| 2013/0073038 A1 | 3/2013 | Azar |
| 2013/0218270 A1 | 8/2013 | Blanckaert et al. |
| 2013/0222756 A1 | 8/2013 | Van Heugten |
| 2014/0085726 A1 | 3/2014 | Portney |
| 2014/0128941 A1* | 5/2014 | Williams ................ A61N 5/06 607/88 |
| 2014/0132904 A1 | 5/2014 | Bos et al. |
| 2014/0156000 A1 | 6/2014 | Campin et al. |
| 2014/0240656 A1 | 8/2014 | Pugh et al. |
| 2015/0057748 A1 | 2/2015 | Azar |
| 2015/0205126 A1 | 7/2015 | Schowengerdt |
| 2015/0362749 A1 | 12/2015 | Biederman et al. |
| 2017/0020660 A1 | 1/2017 | Hyde et al. |

OTHER PUBLICATIONS

PCT International Search Report; International App. No. PCT/US2016/043065; dated Nov. 4, 2016; pp. 1-3.
PCT International Search Report; International App. No. PCT/US2016/043068; dated Oct. 12, 2016; pp. 1-4

* cited by examiner

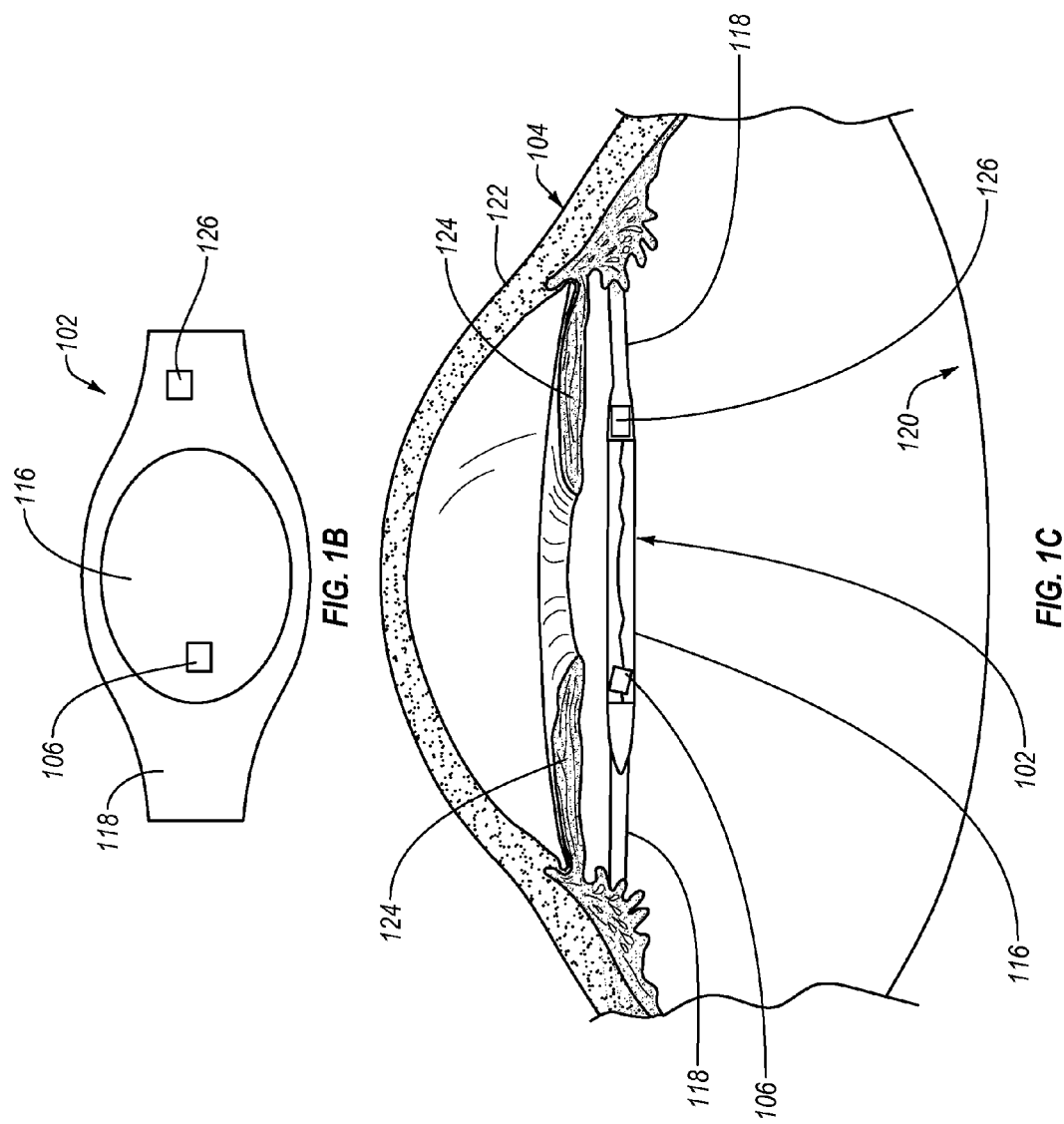

INTRAOCULAR LENS SYSTEMS AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Intraocular lenses (IOLs), such as pseudophakic IOLs, aphikic IOLs, or phakic IOLs (PIOLS), can be used to correct the vision of a subject. Typical IOLs can include monofocal, multifocal, or accommodative configurations. IOLs can include an optic element (e.g., lens) and haptic elements (e.g., arms or wings configured to aid in positioning the IOL).

Such configurations can be limited to focusing either on near or far vision without selectively modifiable adjustment therebetween. Therefore, manufacturers, users, and designers of IOLs continue to seek improved IOLs.

SUMMARY

Embodiments disclosed herein are directed to IOL systems including at least one IOL device and methods of using the same. The at least one IOL device includes one or more photodetectors and an IOL exhibiting a selectable or modifiable focal length. The IOL system can modify the focal length of the IOL responsive to the detected light by the one or more photodetectors.

In an embodiment, an IOL system is disclosed. The IOL system includes at least one IOL device configured to be intraocularly implanted in at least one eye of a subject. The at least one IOL device includes an IOL exhibiting a modifiable focal length. The at least one IOL device also includes one or more photodetectors configured to output one or more detection signals responsive to detecting light. The IOL system further includes a controller configured to be at least one of communicably coupled or operatively coupled to the at least one IOL device. The controller is configured to receive the one or more detection signals from the one or more photodetectors. The controller additionally includes electrical circuitry configured to direct the at least one IOL device to controllably modify the modifiable focal length of the IOL responsive to the one or more detection signals.

In an embodiment, a method of modifying a focal length of an IOL device is disclosed. The method includes, at one or more eyes of a subject, receiving light wherein the one or more eyes include the IOL device. The IOL device includes one or more photodetectors and an IOL exhibiting a modifiable focal length. The method further includes, with the one or more photodetectors, detecting the light and outputting one or more detection signals responsive to the detecting. The method additionally includes, with a controller, controllably changing the modifiable focal length of the IOL responsive to the one or more detection signals.

In an embodiment, an IOL system is disclosed. The IOL system includes a first IOL device configured to be implanted in a first eye of a subject. The first IOL device includes a first IOL exhibiting a modifiable focal length. The first IOL device includes one or more first sensors configured to determine information associated with an angular orientation of the first eye and output one or more first orientation signals responsive to the information. The first IOL device further includes a first communication device. The IOL system also includes a second IOL device configured to be implanted in a second eye of the subject. The second IOL device includes a second IOL exhibiting a modifiable focal length. The second IOL device includes one or more second sensors configured to determine information associated with an angular orientation of the second eye and output one or more second orientation signals responsive the information. The second IOL device further includes a second communication device configured to operably couple the second communication device to the first communication device. The IOL system additionally includes a controller operably coupled to each of the first IOL device and the second IOL device. The controller is configured to receive the one or more first orientation signals from the one or more first sensors of the first IOL device and the one or more second detection signals from the one or more second sensors of the second IOL device. The controller includes electrical circuitry configured to direct each of the first IOL device and the second IOL device to controllably modify the modifiable focal length of the respective IOLs thereof responsive to the one or more first orientation signals and the one or more second orientation signals.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1B is a front view of an IOL, according to an embodiment.

FIG. 1C is a side, cross-sectional view of an eye with an IOL implanted therein, according to an embodiment.

DETAILED DESCRIPTION

Figure 1A:
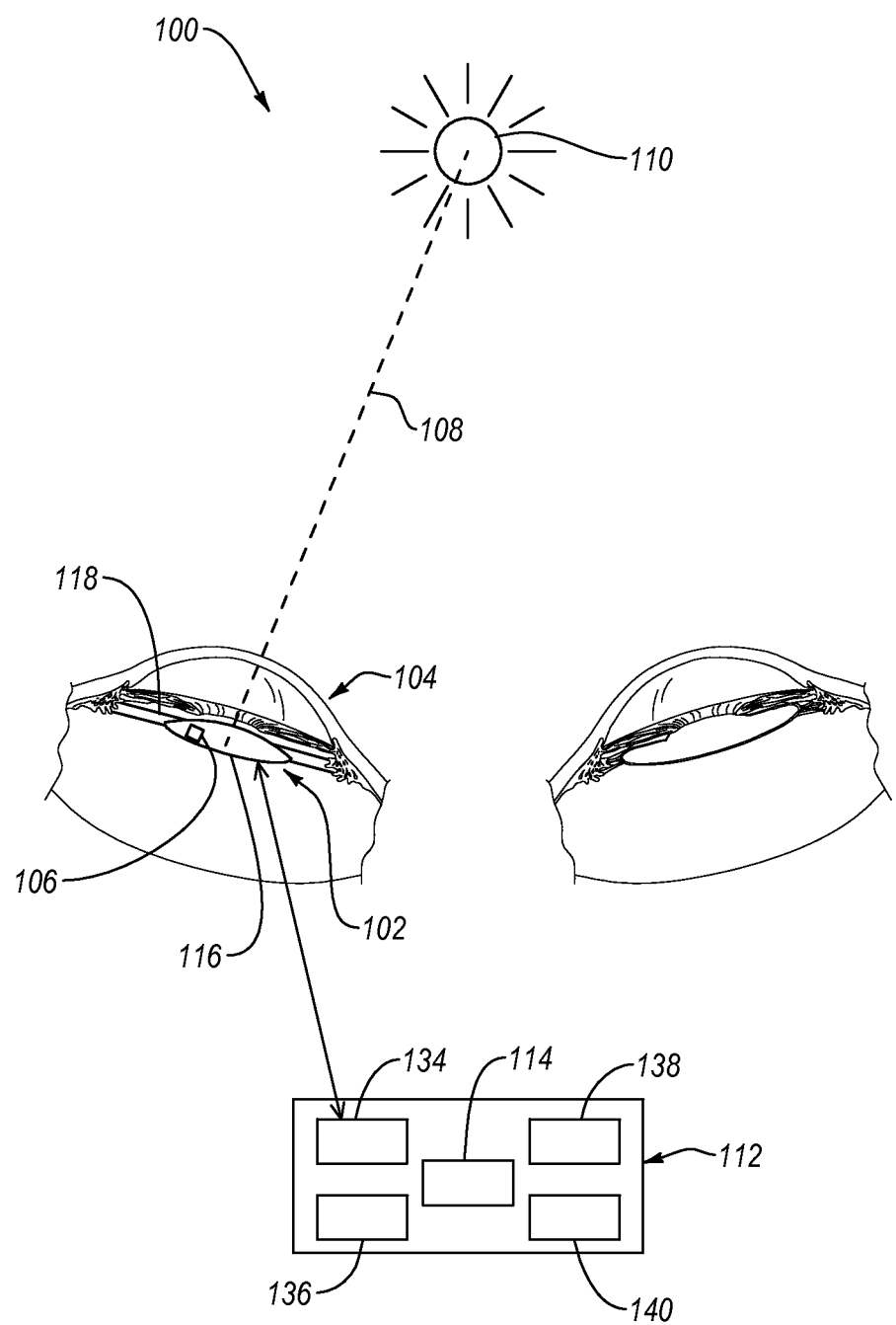
FIG. 1A is a schematic illustration of an IOL system, according to an embodiment.

Embodiments disclosed herein are directed to IOL systems including at least one IOL device and methods of using the same. The at least one IOL device includes one or more photodetectors and an IOL exhibiting a modifiable focal length. The one or more photodetectors are configured to detect light (e.g., electromagnetic radiation), and the IOL system can modify the focal length of the IOL responsive to the detected light, such as presence of an object or apparent object distance.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

The IOL devices and IOL systems disclosed herein can provide a selectively modifiable lens having a selectively modifiable focal length. The IOL devices disclosed herein can include one or more photodetectors configured to detect light. Detecting the light enables the IOL system to determine a position of an object relative to the one or more photodetectors, the IOL, or the eye (e.g., the apparent object distance) or indicate the presence of the object. The object can be any item that a subject desires to view, such as a monitor, television, or e-reader. The light can be transmitted from the object or can be transmitted from a location having a known position relative to the object. When the one or more photodetectors detect the light, the one or more photodetectors can output one or more detection signals. The one or more detection signals can include or can be used to determine an angular position of the light or angular range of the light relative the IOL device (e.g., the one or more photodetectors). The IOL system can determine the apparent object distance or presence of the object using the one or more detection signals. If the IOL system determines that the apparent object distance or the presence of the object requires the lens of the IOL device to exhibit a different focal length to improve visibility of the object to the subject, the IOL system can selectively change the focal length of the IOL responsive to the one or more detection signals.

FIG. 1A is a schematic illustration of an IOL system 100, according to an embodiment. The IOL system 100 includes at least one IOL device 102 (e.g. a single IOL device or multiple IOL devices). In use, the IOL device 102 is implanted into an eye 104 of a subject. The IOL device 102 device includes a lens 116 configured to provide a selectable or modifiable focal length. The IOL device 102 further includes one or more photodetectors 106 configured to detect light 108. Each of the one or more photodetectors 106 can output one or more detection signals responsive to detecting the light 108. The IOL system 100 further includes at least one light source 110 configured to emit the light 108.

The IOL system 100 furthers include a controller 112 operably coupled to the IOL device 102. The controller 112 can be externally carried or worn by the subject or alternatively implanted internally in the subject, such as located in the IOL device 102. The controller 112 includes control electrical circuitry 114. The control electrical circuitry 114 can receive the one or more detection signals either directly or indirectly from the one or more photodetectors 106 and determine a presence of an object from which the light 108 emanates or a position of the at least one light source 110 relative to the one or more photodetectors 106, the eye 104, or the IOL device 102. The control electrical circuitry 114 can direct the IOL device 102 to select or modify a focal length of the lens 116 responsive to the determined presence or position.

FIG. 1B is a front view of the IOL device 102, according to an embodiment. The IOL device 102 is configured to fit in or on one or more anatomical structures of the eye 104. As such, the IOL device 102 can include one or more haptics 118. The lens 116 can be configured to focus light onto a surface of a retina 120 of the subject to correct or augment the vision of the subject. The lens 116 can be configured to exhibit a modifiable focal length using, for example, one or more switchable diffractive lenses or one or more switchable refractive lenses. The lens 116 can be configured to augment or correct visual deficiencies of the subject or to replace a natural lens of the subject, such as in the case of cataract surgeries. As shown in FIG. 1B, the one or more haptics 118 can be configured as wings extending away from the lens 116. In an embodiments, the one or more haptics 118 can be configured as arms or struts having an elbow or bend therein. The arms can be similar to the wings shown in FIG. 1B, with one or more portions of a center of the wings removed therefrom.

The one or more photodetectors 106 can be positioned on a portion of the IOL device 102 that receives the light 108. In an embodiment, the one or more photodetectors 106 can be positioned in or on the lens 116. For example, the one or more photodetectors 106 can be positioned such that the one or more photodetectors are substantially out of focus at the retina 120 of the eye 104. In an embodiment, the one or more photodetectors 106 can be positioned in the one or more haptics 118. Additionally, the IOL device 102 can further include one or more portions 126 configured to have one or more components of the IOL system 100 (e.g., the first communication device 128 shown in FIG. 1D) positioned therein or thereon. For example, the one or more portions 126 can be positioned in the lens 116 or the haptic 118.

FIG. 1C is a side, cross-sectional view of the eye 104 with the IOL device 102 implanted therein, according to an embodiment. The eye 104 can include a cornea 122, an iris 124, and the retina 120 therebehind. The at least one IOL device 102 can be implanted in the eye 104. In the illustrated embodiment, the IOL device 102 can replace the natural lens of the eye 104. However, in other embodiments, the eye 104 can include both the IOL device 102 and the natural lens (not shown). For example, the IOL device 102 can be implanted over the natural lens of the eye 104, in front of (e.g., in the anterior chamber) the iris 124, behind the iris 124 (e.g., in the posterior chamber or the posterior cavity), or internal to the natural lens such as in the capsular bag of the natural lens. In an embodiment, the natural lens can be absent from the eye 104 (e.g., the IOL device 102 can replace the natural lens and can be placed in the anterior chamber, the posterior chamber, or internal to the capsular bag that is used to contain the natural lens). In an embodiment, the one or more haptics 118 can be positioned on a ciliary body or muscles or in or on the capsular bag of the natural lens. The lens 116 can be located laterally at or near a center of the eye 104, with the one or more haptics 118 extending laterally therefrom. The IOL device 102 and, specifically the lens 116, can be configured to exhibit a modifiable focal length.

Referring again to FIG. 1A, the one or more photodetectors 106 are configured to detect the light 108. In an embodiment, the light 108 can be configured to be distinguishable from ambient light or light from common sources. The one or more photodetectors 106 can be configured to detect and distinguish the light 108 due to the light 108 possessing certain selected characteristics, such as a selected wavelength(s), selected angular beamwidth, selected amplitude(s), or selected polarization. In an embodiment, the one or more photodetectors 106 can be configured to detect the light 108 that pulsates in a selected waveform. For example, the light 108 can pulsate at a selected frequency, in a selected pattern (e.g., the light 108 is emitted in an ABABAB pattern, where A has a first frequency and B has a second frequency), or a predictable pattern (e.g. a recognizable pattern or a repetitive pattern). To avoid confusion herein, light will be characterized in terms of wavelength, while the rate the light is pulsated will be characterized in terms of frequency. In an embodiment, the one or more photodetectors 106 can be configured to receive information encoded in the light 108. For example the light source 110 can encode information, such as the location of the light source 110 relative an object, in the light 108 (e.g., optical wireless communication). The one or more photodetectors 106 can be configured to receive both the light 108 and the information encoded therein.

The one or more photodetectors 106 or any of the photodetectors used in any of the embodiments disclosed herein can be any suitable photodetectors configured to detect the light 108. For example, the one or more photodetectors 106 or any of the photodetectors used in any of the embodiments disclosed herein can include one or more optical detectors, one or more photodiodes, or other suitable photodetector. In an embodiment, the one or more photodetectors 106 or any of the photodetectors used in any of the embodiments disclosed herein can include an active-pixel sensor or a charge-coupled device. In an embodiment, the one or more photodetectors 106 or any of the photodetectors used in any of the embodiments disclosed herein can include an image plate, such as a photostimulatable phosphor plate. In an embodiment, the one or more photodetectors 106 or any of the photodetectors used in any of the embodiments disclosed herein can include a flat panel detector, such as an indirect flat panel detector or a direct flat panel detector. In an embodiment, the one or more photodetectors 106 or any of the photodetectors used in any of the embodiments disclosed herein can include one photodiode or a plurality of photodiodes. The photodiode can include a photoconductive diode, an avalanche photodiode, a phototransistor, or other suitable photodiode. In an embodiment, the one or more photodetectors 106 or any of the photodetectors used in any of the embodiments disclosed herein can include a thermometer configured to detect the light 108 (e.g., the thermometer absorbs the light 108 and detects the resulting heat generated thereby). Such thermometers can include pyroelectric detectors and bolometers. In an embodiment, the one or more photodetectors 106 can include a photoresistor.

In an embodiment, the one or more photodetectors 106 can be configured to detect the light 108 having a specific wavelength or range of wavelengths. The type of photodetector 106 used to detect the light 108 can depend on the wavelength of the light 108 to be detected. In an embodiment, the one or more photodetectors 106 can be configured to detect light having a wavelength of about 0.01 nm to about 10 nm (e.g., x-rays). In such an embodiment, the one or more photodetectors 106 can include an image plate or a flat panel detector. In an embodiment, the one or more photodetectors 106 can be configured to detect the light 108 having a wavelength of about 10 nm to about 400 nm (e.g., ultraviolet light). In an embodiment, the one or more photodetectors 106 can be configured to detect the light 108 having a wavelength of about 400 nm to about 700 nm (e.g., visible light). In such an embodiment, the one or more photodetectors 106 can include active-pixel sensors, charge-coupled device, photodiodes, or other photodetectors disclosed herein. In an embodiment, the one or more photodetectors 106 can be configured to detect the light 108 having a wavelength of about 0.75 μm to about 1.4 μm (e.g., near-infrared), about 1.4 μm to about 3 μm (short-wavelength infrared), about 3 to about 8 μm (e.g., mid-wavelength infrared), about 8 μm to about 15 μm (e.g., long-wavelength infrared) or 15 μm to about 1000 μm (e.g., far-infrared). In such an embodiment, the one or more photodetectors 106 can include photodiodes, photo resisters, or other photodetectors disclosed herein. In an embodiment, the one or more photodetectors 106 can be configured to detect the light 108 having a wavelength of about 1 mm to about 1 m (e.g., microwave). For example, the one or more photodetectors can be configured to detect light having a wavelength of about 1 mm to about 10 mm (e.g., extremely high frequency microwave spectrum), such as about 1.8 mm to about 2.7 mm, about 2.1 mm to about 3.33 mm, about 2.7 mm to about 4.0 mm, about 4.0 mm to about 4.0 mm, or about 5.0 mm to about 7.5 mm. In such and embodiment, the one or more photodetectors 106 can include a semiconductor diode or a semiconductor transistor. In an embodiment, the one or more photodetectors 106 can be configured to detect a combination of any of the wavelengths disclosed herein.

In an embodiment, the one or more photodetectors 106 can include a coating applied thereto that is at least partially to fully transparent to the light 108. For example, the one or more photodetectors 106 can include a lead sulphide photoresistor. The lead sulphide photoresistor can be configured to detect mid-infrared light. The lead sulphide photoresistor can be coated with a biocompatible coating due to the lead sulphide photoresistor's toxicity. The biocompatible coating can be at least partially transparent to mid-infrared light. The biocompatible coating can be configured to be at least semi-impermeable (e.g., substantially impermeable or impermeable) to the lead sulphide.

The one or more photodetectors 106 are configured to receive and detect the light 108. However, the one or more photodetectors 106 can also receive and detect background or ambient light (e.g., light other than the light 108). In an embodiment, the IOL system 100 can include can include one or more filters (not shown) configured to limit an amount of background light that reaches or is absorbed by the one or more photodetectors 106. The one or more filters can enable the IOL system 100 (e.g., the one or more photodetectors 106) to distinguish between the light 108 and the background light. In an embodiment, the one or more filters can be at least partially transparent to the light 108, while being at least partially opaque to at least some of the background light. For example, the one or more filters can be at least partially transparent to infrared light. Filters that are at least partially transparent to infrared light include, for example, chalcogenide glass, cadmium telluride, gallium arsenide, germanium, silicon, or other applicable materials. In an embodiment, the one or more filters can be at least partially transparent to ultraviolet light. Filters that are at least partially transparent to ultraviolet light include fused silica and calcium fluoride. In other embodiments, the one or more filters can be at least partially transparent to visible light, microwaves and other wavelengths. In an embodiment, the one or more filters can include a plurality of materials where the plurality of materials combined are at least partially transparent to a narrower range of wavelengths of light than each material individually. In an embodiment, the one or more filters can include one or more polarizers. For example, the IOL system 100 can include two polarizers oriented such that only light having a specific polarization reaches the one or more photodetectors 106.

In operation, the light 108 enables the IOL system 100 to determine a presence of the object (not shown) or determine the apparent object distance. In an embodiment, the object can be an item that the subject views or can be an object that has a relationship to said item. For example, the object can be a television, a wall, a ceiling, a work surface, eyeglasses, a monitor, an e-reader, a tablet, a cellphone, a laptop computer, a desktop computer, a reading light, etc. In an embodiment, the light 108 comes directly from the object. For example, a television screen can include the at least one light source 110 that emits the light 108. In an embodiment, the at least one light source 110 can be attached to or incorporated into the object. As such, detecting or determining the angular position of the light 108 relative to the one or more photodetectors 106 or IOL device 102 can determine the angular position of the object relative to one or more photodetectors 106, the IOL device 102, or the eye 104. In an embodiment, the light 108 comes from a location that is remote from the object. However, the at least one light source 110 can have a known position relative to the object.

In an embodiment, the light 108 can be emitted by the at least one light source 110. Generally, the at least one light source 110 is configured to emit the light 108 at a selected wavelength or range of wavelengths such as, about 0.01 nm to about 10 nm (e.g., x-rays), about 10 nm to about 400 nm (e.g., ultraviolet light), about 400 nm to about 700 nm (e.g., visible light), about 0.75 µm to about 1.4 µm (e.g., near-infrared), about 1.4 µm to about 3 µm (short-wavelength infrared), about 3 to about 8 µm (e.g., mid-wavelength infrared), about 8 µm to about 15 µm (e.g., long-wavelength infrared), or 15 µm to about 1000 µm (e.g., far-infrared). For example, the at least one light source 110 can include one or more light emitting devices such as, at least one of an incandescent lamp, a light emitting diode (LED), an arc lamp, a laser, or a gas discharge lamp.

In an embodiment, the at least one light source 110 can be configured to emit the light 108 having a selected wavelength, a range of selected wavelengths, a selected amplitude, or range of selected amplitudes. For example, the at least one light source 110 can include a xenon arc lamp. In such an embodiment, the amplitude of the at least one light source 110 can be dependent on the wattage or power of the xenon arc lamp. Additionally, the light 108 emitted by the xenon arc lamp includes strong emissions of light of about 450 nm to about 500 nm and about 825 nm to about 925 nm. As such, the one or more photodetectors 106 can be configured to detect the light 108 having the above characteristics. In an embodiment, the at least one light source 110 can include a polarizer such that the light source 110 emits the light 108 having a selected polarization. In an embodiment, the at least one light source 110 can be configured to emit the light 108 in pulses having a selected frequency, a selected pattern, or selected pattern.

As previously discussed, each of the one or more photodetectors 106 outputs the one or more detection signals responsive to detecting the light 108. The one or more detection signals can include or be used to determine the presence of the object, or the angular position or angular range of the light 108 relative to the one or more photodetectors 106 or the IOL device 102. In an embodiment, the one or more photodetectors 106 detect the light 108 that is at least partially occluded by one or more objects having a known location relative the photodetector 106. As such, the light 108 does not illuminate the entire one or more photodetectors 106. For example, the light 108 can be at least partially occluded by one or more structures of the eye (e.g., the iris 124), one or more anatomical features of the subject (e.g., the nose), one or more structures internally positioned within the IOL device 102 (e.g. the first communication device 128), or one or more structures externally spaced from the IOL device 102 (e.g., eyeglass frames). As such, the one or more photodetectors 106 can output the one or more detection signals including information detailing how the light was occluded. In an embodiment, the one or more photodetectors 106 can be configured to detect the light 108 at a certain angular direction or angular range relative to the one or more photodetectors 106. As such, the one or more detection signals can merely include that the one or more photodetectors 106 detected the light 108. In an embodiment, the one or more photodetectors 106 can detect the light at a plurality of angular positions or angular ranges simultaneously (e.g., an active-pixel array). As such, the one or more detection signals can include information about light detected in a plurality of angular positions or angular ranges. In an embodiment, the one or more photodetectors 106 can include a plurality of photodetectors 106, such as a first photodetector and at least a second photodetector. The first photodetector and the second photodetector can be configured to detect the light 108 substantially simultaneously. The angular direction of the light 108 detected by the first photodetector can be different than the angular direction of the light 108 detected by the second photodetector. As such, the one or more detection signals outputted by the first photodetector can be different from the one or more detection signals outputted by the second photodetector. In an embodiment, the one or more photodetectors 102 can detect an amplitude or an intensity of the light 108. As such, the one or more detection signal outputted by the one or more photodetectors can include the amplitude or intensity of the light 108.

Figure 1D:
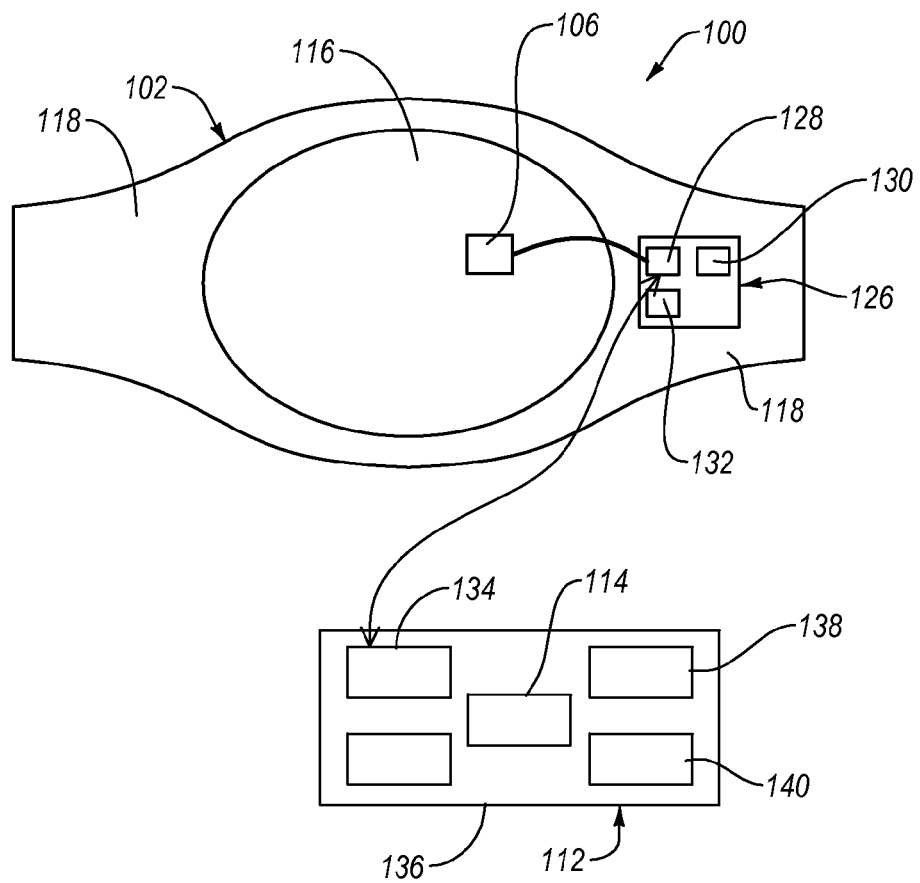
FIG. 1D is a schematic illustration of a portion of an IOL system, according to an embodiment.

FIG. 1D is a schematic illustration of a portion of the IOL system 100, according to an embodiment. In the illustrated embodiment, the one or more portions 126 of the IOL device 102 are configured to have one or more components of the IOL system 100 positioned therein. For example, each of the one or more portions 126 can be configured to have a single component or a plurality of components positioned therein or thereon. In an embodiment, the one or more portions 126 can be positioned in the lens 116 or one or the haptics 118. For example, if the one or more portions 126 are positioned in the lens 116, the one or more portions 126 can be positioned to be substantially out of focus at the retina 120 of the subject.

In an embodiment, the IOL system 100 can include a first communication device 128 positioned in the one or more portions 126. The first communication device 128 can communicably couple the IOL device 102 to another component of the IOL system 100, such as the controller 112. The first communication device 128 can be configured to transmit one or more communication signals to the controller 112. The one or more communication signals can include at least a portion of or information about the one or more detection signals. Additionally, the first communication device 128 can be configured to receive one or more control signals from the controller 112. The one or more control signals can include at least one direction from the control electrical circuitry 114. As such, the first communication device 128 can include an antenna, such as embodied in a transceiver. In an embodiment, the first communication device 128 can be communicably coupled to the one or more photodetectors 106 to receive the one or more detection signals therefrom.

In an embodiment, the IOL system 100 can include IOL electrical circuitry 130 positioned in the one or more portions 126. The IOL electrical circuitry 130 can be configured to process information, distribute information, distribute energy, or control one or more components of the IOL system 100. In an embodiment, the IOL electrical circuitry 130 can receive the one or more detection signals from the one or more photodetectors 106. The IOL electrical circuitry 130 can then digitize the one or more detection signals to generate the one or more communication signals. The IOL electrical circuitry 130 can then output the one or more communication signals to the first communication device 128, with directions to transmit the one or more communication signals to the controller 112. In an embodiment, the IOL electrical circuitry 130 can receive the one or more control signals from the first communication device 128 and can execute the at least one direction contained or encoded in the one or more control signals.

Figure 1E:
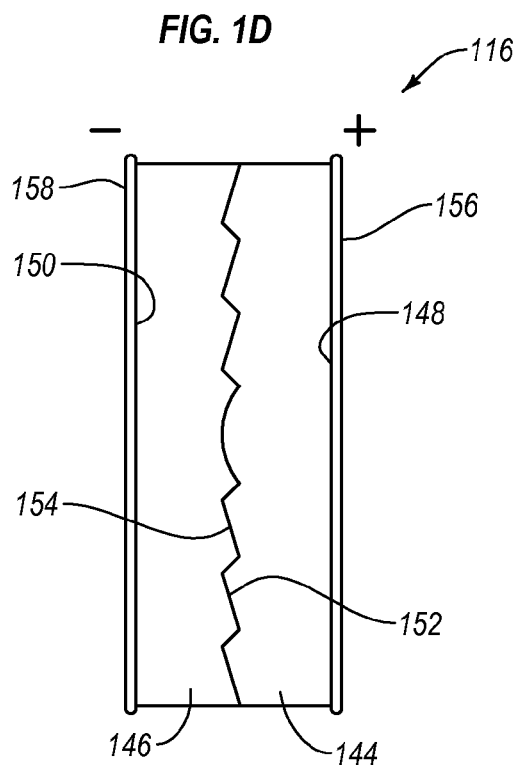
FIG. 1E is a side, cross-sectional view of a portion of a switchable diffractive lens, according to an embodiment.

In an embodiment, the IOL system 100 can include a power source 132 positioned in the one or more portions 126. The power source 132 can be configured to deliver electrical power to one or more components of the IOL device 102. For example, the power source 132 can power the first communication device 128, the IOL electrical circuitry 130, the one or more photodetectors 106 (if needed), or a mechanism that modifies the focal length of the lens 116 (e.g., the first electrode 156 or the second electrode 158 as shown in FIG. 1E). In an embodiment, the power source 132 can include a micro-battery or any other battery having a suitably small size to fit into the IOL system 100. Suitable batteries can include a thin film battery, a button cell battery, or any other miniaturized battery. A suitable thin film battery can include a flexible thin film lithium-ion battery, such as the LiTe*STAR™ thin-film rechargeable battery or Thinergy® battery by Infinite Power Solutions, or equivalents thereof. The battery can be configured to deliver 0.1 mV or more, such as about 0.1 mV to about 20 V, about 0.5 mV to about 5 V, about 0.5 V, about 1 V, about 2 V, or about 10 V or less. The battery can be configured to deliver 0.1 mA or more, such as about 0.1 mA to about 1 A, about 0.2 mA to about 0.5 mA, or about 1 A. In an embodiment the power source 132 can include a sufficiently small thermoelectric device (e.g., thermoelectric generator) configured to charge a battery or capacitor via heat harvested through the thermoelectric device. In an embodiment, the power source 132 can include an induction coil configured to produce current from a changing magnetic field applied thereto. The induction coil can be configured to charge a battery or capacitor. In an embodiment, the power source 132 can include the one or more photodetectors 106 configured to generate electricity (e.g., a photovoltaic cell). The power source 132 can include any other suitably sized device capable of providing an electrical charge.

In an embodiment, the power source 132 may include a parasitic power device, such as an induction coil, thermoelectric device, or any other device configured to harvest energy from a subject. For example, the induction coil can include a channel having a magnet therein, the channel passing the induction coil upon movement of the subject (e.g., eye-movement or blinking) In an embodiment, an induction coil can be disposed in the eye of a subject (e.g., in or adjacent to the IOL) and a corresponding magnet may be positioned on an adjacent part of the subject (e.g., an eyelid or bridge of the nose) whereby movement of the eye or eyelid can cause a current in the induction coil.

The controller 112 is communicably coupled, either directly (e.g., the controller 112 is positioned in the IOL device 102) or indirectly (e.g., via the first communication device 128), to at least one of the one or more photodetectors 106, the lens 116, the first communication device 128, or the IOL electrical circuitry 130. The controller 112 can be communicably coupled through a wired or wireless (e.g., Bluetooth, Wi-Fi) connection. In an embodiment, the controller 112 can be positioned in the IOL device 102 (e.g., in the one or more portions 126). In an embodiment, the controller 112 is positioned remotely from the IOL device 102, such as worn externally by the subject.

In an embodiment, the controller 112 can include a second communication device 134. The second communication device 134 can communicably couple the controller 112 to the IOL device 102 or another component of the IOL system 100 that is remote from the controller 112. The second communication device 134 can be configured to receive the one or more communication signals from the first communication device 128. Additionally, the second communication device 134 can be configured to transmit one or more control signals to the first communication device 128. As such, the second communication device 134 can include an antenna, such as embodied as a transceiver or a receiver.

In an embodiment, the controller 112 can include a user interface 136 that enables an individual (e.g. the subject) to communicate with the IOL system 100. The user interface 136 can include a display, touch screen, microphone, speaker, or any other device that enables the individual to communicate with the IOL system 100. The user interface 136 can also include software that enables the individual to communicate with the IOL system 100, such as an operating system, operator controls or a process control. For example, the user interface 136 is configured to enable an individual to access the controller 112 via a computer or personal electronic device to allow the individual to selectively configure the IOL system 100, as desired or needed. In an embodiment, the user interface 136 can enable an individual to input instructions or commands into the IOL system 100. The commands can include instructions on how to determine the apparent object distance, the focal lengths that the lens 116 can exhibit, the position of the at least one light source 110 relative to the object, etc. In an embodiment, the IOL system 100 can send data to the user interface 136. The data can include information about the current focal length of the lens 116, how often the IOL device 102 modifies the focal length of the lens 116, the current status of the power source 132, etc. The user interface 136 can display the data. Additionally, the user interface 136 can be used to calibrate the IOL system 100.

The controller 112 can further include memory 138 storing operational instructions for operating the IOL system 100. The memory 138 can include random access memory (RAM), read only memory (ROM), a hard drive, a disc (e.g., blue-ray, DVD, or compact disc), flash memory, other types of memory electrical circuitry, or other suitable memory. The instructions stored on the memory 138 can include the possible focal lengths of the lens 116, methods to determine when to modify the focal length of the lens 116, the position of the light source 110 relative to the object, etc. The controller 112 can further include a processor 140 configured to direct certain operations of the IOL system 100 according to the instructions contained in the memory 138.

As previously discussed, the controller 112 includes the control electrical circuitry 114. The control electrical circuitry 114 receives the one or more detection signals either directly or indirectly. For example, the control electrical circuitry 114 can receive the one or more communication signals from the second communication device 134 and can extract at least a portion of the one or more detection signals from the one or more communication signals. The control electrical circuitry 114 can direct the IOL device 102 to modify a focal length of the lens 116 responsive to the one or more communication signals. For example, the focal length can be shorted responsive to the one or more communication signals indicating the presence of the object or the apparent distance of the object. In an embodiment, the control electrical circuitry 114 can distinguish between the light 108 and the background light based on the selected wavelength(s), selected amplitude(s), selected angular beamwidth, or selected polarization of the light 108 relative to the background light. As another example, when the controller 112 is disposed on or in the one or more portions 126, the first and second communication devices 128 and 134 can be omitted, and the control electrical circuitry 114 can receive the one or more detection signals directly from the one or more photodetectors 106.

The control electrical circuitry 114 analyzes the one or more detection signals to determine the presence or the position of apparent object distance. In an embodiment, the IOL system 100 includes a single photodetector 106 and a single light source 110. In such an embodiment, the control electrical circuitry 114 can estimate the apparent object distance using the angular position of the light 108. In an embodiment, the IOL system 100 can include a plurality of photodetectors 106 spaced from each other in the form of an array having a known or selected spacing between the individual photodetectors 106. In such an embodiment, the control electrical circuitry 114 can determine the apparent object distance by comparing the angular position of the light 108 relative to each of the plurality of photodetectors 106. For example, the light 108 from a relatively compact and distant light source 110 (which does not have to be associated with an object being intentionally viewed by the subject) can be received by a lens or mirror located within the IOL and focused onto a photodetector array. The identification of which of the photodetectors 106 within the array receive the focused light can then determine the direction of the incident light relative to the IOL and, hence, the orientation of the eye (containing the IOL) relative to the incident light. The control electrical circuitry 114 can compare eye orientations of both eyes to determine the presence and value of a vergence angle between the two eyes and distinguish vergence from a common co-tilt of each eye (e.g., towards a peripheral object). Knowledge of a vergence angle can then be used by the control electrical circuitry 114 to determine a convergence distance of the two eyes and, hence, a distance towards a nearby object being viewed by the two eyes. This object distance can then be used to determine a desired focal length of the lens 116. In an embodiment, the IOL system 100 can include a plurality of light sources 110 spaced from each other. Each of the light sources 110 can have a known position relative to the object and can be configured to emit a light 108. Additionally, each of the plurality of light sources 110 can be configured to emit a light 108 that is distinguishable from a light 108 emitted by another light source 110. Each of the one or more photodetectors 106 can detect the angular position or angular range of each of the plurality of light sources 110. The control electrical circuitry 114 can determine the apparent object distance using the detected angular position or angular range of each of the plurality of light sources 110. In an embodiment, the one or more photodetectors 106 can be configured to detect the amplitude or intensity of the light 108. In such an embodiment, the control electrical circuitry 114 can determine or correlate the apparent object distance using the detected amplitude or intensity of the light 108 if the amplitude or intensity of the light 108 emitted by the light source 110 is known. For example, if the detected amplitude or intensity of the light 108 indicates that the object is relatively close, the control circuitry 114 can direct the lens 116 to modify the focal length thereof to relatively shorter to improve visibility of the object to the subject. In an embodiment, the control electrical circuitry 114 can be configured to determine the apparent object distance using any suitable mathematical (e.g., trigonometric) or optical method known in the art. The control electrical circuitry 114 can determine and controllably change the focal length the lens 116 based on apparent object distance as determined by the control electrical circuitry 114. For example, if the control electrical circuitry 114 determines that the object is relatively proximate to the IOL device 102 (e.g., near focus), the control electrical circuitry 114 can controllably change the focal length of the lens 116 to exhibit a relatively short focal length.

In an embodiment, the control electrical circuitry 114 can be integrally formed with the memory 138 and the processor 140 of the controller 112. Alternatively, the control electrical circuitry 114 can be separate from the memory 138 and the processor 140 of the controller 112. In such an embodiment, the control electrical circuitry 114 can include its own memory and processor.

The lens 116 of the IOL device 102 can include any suitable lens that is configured to modify the focal length thereof (e.g., optical power). In an embodiment, the lens 116 can include a switchable lens that can switch between distinct focal lengths. For example, a switchable lens can switch between at least a first focal length and a second focal length, where the second focal length is different (e.g., greater) than the first focal length. In an embodiment, the lens 116 can include a switchable diffractive lens. A switchable diffractive lens is any lens that includes a diffractive lens and can switch its focal length between at least a first focal length and a second focal length. The switchable lens can include any suitable switchable diffractive lens.

In an embodiment, the lens 116 can include a variable focus refractive lens. A variable focus refractive lens includes any lens that modifies a focal length thereof by changing an index of refraction of the lens. In an embodiment, the lens 116 can include a lens that changes a focal length thereof by physically modifying the shape of the lens.

In an embodiments, the IOL system 100 or any IOL system disclosed herein can include one or more sensors (not shown) configured to detect one or more physiological indicia of the subject. For example, the IOL system can include one or more sensors configured to detect glucose concentration, such as in the eye of the subject; eye pressure, heart rate, biological proteins present in the eye, or any other biological indicia using any suitable technique. The one or more sensors can be operably coupled to the control electrical circuitry, such as control electrical circuitry 114. The control electrical circuitry of the IOL system 100 or other IOL system can be configured to transmit the measurements of the physical indicia to a remote source such as a computer, a cellular phone, or other electronic device. In an embodiment, the measured physical indicia may be used to determine the health of a subject or eye thereof, customize the operation of the lens to the particular subject, determine if the lens needs to be removed or adjusted, or determine if the focal adjustments of the lens are suitable for the subject. The electronic device may then transmit instructions to the control electrical circuitry to selectively control or otherwise adjust the functioning of the IOL system, such as controllably changing the focal length of the lens 116.

FIG. 1E is a side, cross-sectional side view of a portion of the lens 116, according to an embodiment. In the embodiment illustrated in FIG. 1E, the lens 116 includes a diffractive lens and one or more materials therein, such as one or more electro-optical materials having an electrically-modifiable index of refraction.

In an embodiment, the one or more materials can include a first material 144 and a second material 146. The first material 144 can include an electro-optical material. Electro-optical materials include those materials having an electrically-modifiable index of refraction (e.g., lithium niobate or lithium tantalite, etc.). Electro-optical materials can be configured to provide a selectively modifiable index of refraction, such as a first, ground state index of refraction and a second, activated index of refraction induce by a stimulus (e.g., electrical stimulus in an electrically-modifiable material) applied thereto. In an embodiment, the second material 146 can include a substantially electro-optically inert material having a substantially fixed index of refraction (e.g., glass). Alternatively, the second material 146 can include an electro-optical material having a selectively modifiable index of refraction, similar to or different from the index of refraction of the first material 144.

The first material 144 can include a first outer surface 148 and the second material 146 can include a second outer surface 150. The first outer surface 148 and the second outer surface 150 can be remote from one another and positioned in generally opposing directions. The first materials 144 can also include a first diffraction surface 152 that is substantially opposite to the first outer surface 148 and defines a first diffraction pattern. The second material 146 can include a second diffraction surface 154 that is substantially opposite to the second outer surface 150 and defines a second diffraction pattern. The second diffraction pattern can be substantially complementary (e.g. a mirror image of) to the first diffraction pattern such that the first and second diffraction surfaces 152 and 154, respectively, can be substantially seamlessly joined together without any gaps therebetween.

In order to provide a sufficient bias (e.g., electrical stimulus) to induce the modified index of refraction in the electro-optical materials, the IOL system 100 can include a first electrode 156 and a second electrode 158. The first electrode 156 can be disposed on the first outer surface 148 and the second electrode 158 can be disposed on the second outer surface 150. The first electrode 156 and the second electrode 158 can be configure to deliver or maintain an electrical bias across the first material 144 and the second material 146 effective to modify the index of refraction of one or both materials therebetween. The first electrode 156 and the second electrode 158 can apply the electrical bias responsive to direction from the control electrical circuitry 114.

In an embodiment, the lens 116 can be modified to switch between a first focal length and a second focal length. For example, in a ground state, the electro-optical material can exhibit a first index of refraction and a first focal length. The lens 116 can be changed into its active state by applying an electric bias. In the active state, the electro-optical material of the lens 116 can exhibit a second index of refraction that is different from the first index of refraction and a second focal length that is different from the first focal length.

In an embodiment, the lens 116 can be configured to be switchable between three or more focal lengths. For example, the lens 116 can be configured to exhibit a first focal length, a second focal length that is greater than the first focal length, and one or more intermediate focal lengths having a magnitude between the first focal length and the second focal length. Examples of lenses that are switchable between three or more focal lengths are disclosed in U.S. patent application Ser. No. 14/807,673 to Roderick A. Hyde, et al. titled "Intraocular Lens Systems and Related Methods" and filed concurrently herewith, the disclosure of which is incorporated herein by this reference, in its entirety.

Figure 1F:
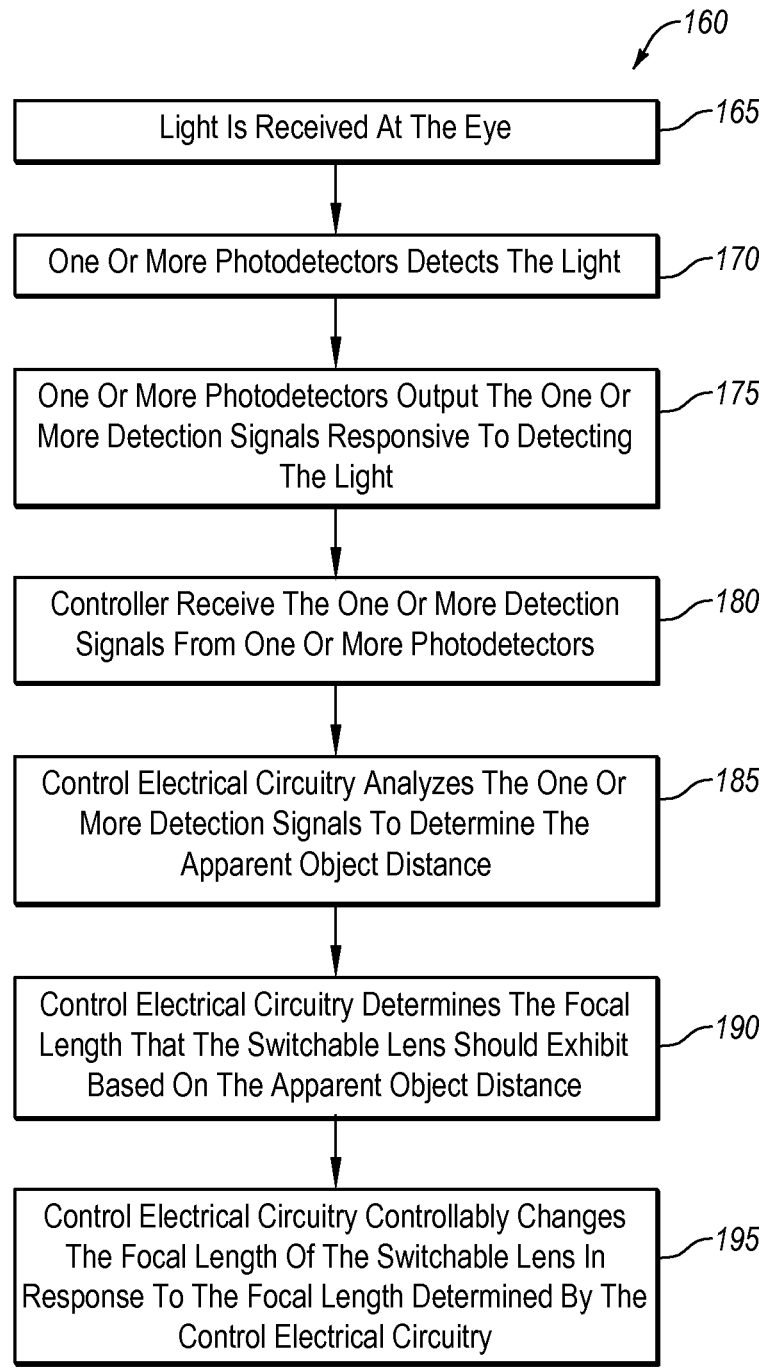
FIG. 1F is a flow diagram illustrating a method of using an IOL system, according to an embodiment.

FIG. 1F is a flow diagram of a method 160 of using the IOL system 100, according to an embodiment. In act 165, the light 108 is received at the eye 104. The light received by the eye 104 enables the IOL system 100 to determine the presence of or the apparent object distance. For example, the light 108 can be emitted by at least one light source 110 attached to the object. The light 108 can have a specific characteristic (e.g., a selected wavelength, selected amplitude, or selected polarization) or can be emitted as a plurality of pluses having a selected frequency or selected pattern that distinguishes the light 108 from background light. In act 170, the one or more photodetectors 106 detects the light 108. In an embodiment, the IOL system 100 can include one or more filters that at least partially prevent background light from reaching the one or more photodetectors 106. However, in other embodiments, the IOL system 100 can allow the one or more photodetectors 106 to receive and detect the light 108 and background light. In act 175, the one or more photodetectors 106 outputs one or more detection signals responsive to detecting the light 108. The one or more detection signals can include or can be used to determine a presence of the object from which the light 108 emanates or an angular position from which the light 108 emanates or the angular range of the light 108 relative to one or more photodetectors 106.

In block 180, the controller 112 can receive the one or more detection signals from the one or more photodetectors 106. For example, the controller 112 can be positioned within the IOL device 102 and can receive the one or more detection signals directly from the one or more photodetectors 106. Alternatively, the controller 112 can be positioned remotely from the IOL device 102. As such, the controller 112 can receive the one or more detection signals from one or more communication signals sent from the IOL device 102 (e.g., via the first communication device 128). In block 185, the control electrical circuitry 114 analyzes the one or more detection signals to determine the presence of the object or the apparent object distance. In block 190, the control electrical circuitry 114 determines the focal length that the lens 116 should exhibit based on the presence of the object or the apparent object distance. In block 195, the control electrical circuitry 114 controllably changes the focal length of the lens 116 responsive to the apparent object distance determined by the control electrical circuitry 114. For example, the controller 112 can transmit a direction from the control electrical circuitry 114 to change the focal length of the lens 116 via the second communication device 134. The IOL electrical circuitry 130 can then change the focal length of the lens 116 responsive to the direction.

Figure 2A:
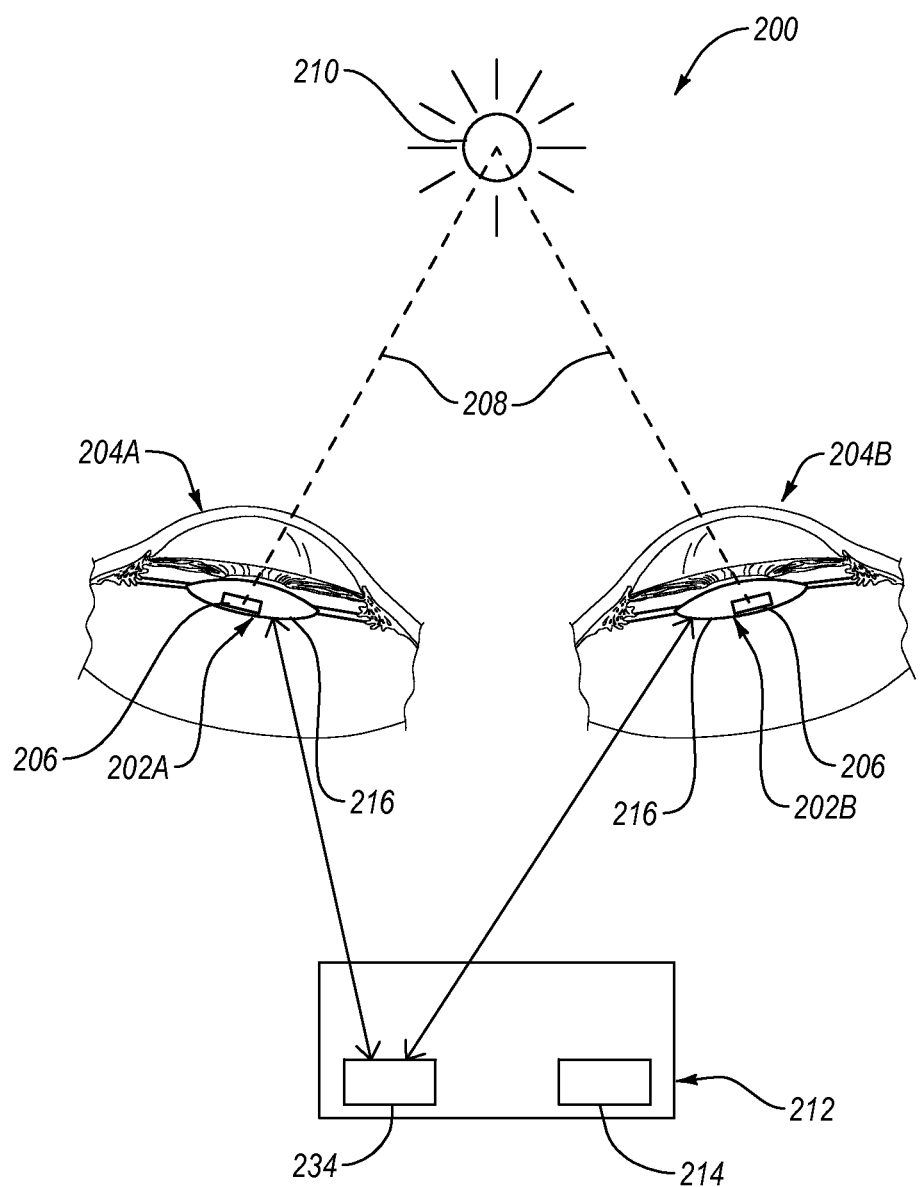
FIG. 2A is a schematic illustration of an IOL system, according to an embodiment.

FIG. 2A is a schematic illustration of an IOL system 200, according to an embodiment. The IOL system 200 includes a first IOL device 202A and a second IOL device 202B. The first IOL device 202A is implanted in a first eye 204A of a subject and the second IOL device 202B is implanted in a second eye 204B of the subject. In an embodiment, each of the first IOL device 202A and the second IOL device 202B are substantially similar to or the same as the IOL device 102 shown in FIG. 1A. For example, the first IOL device 202A and the second IOL device 202B can each include a lens 216 that has a modifiable focal length, such as any of the lenses disclosed herein. The first IOL device 202A and the second IOL device 202B can further include one or more photodetectors 206 configured to detect light 208. In an embodiment, the light 208 can be emitted by a light source 210 having a known position relative to an object (not shown). Each of the one or more photodetectors 206 outputs one or more detection signals responsive to detecting the light 208. The one or more detection signals can include or be used to determine an angular position of the light source 210 relative to one or more photodetectors 106. The IOL system 200 further includes a controller 212 communicably coupled to and spaced from the first IOL device 202A and the second IOL device 202B. The controller 212 includes control electrical circuitry 214 that can receive the one or more detection signals and determine the apparent object distance. The control electrical circuitry 114 can direct the first IOL device 202A or the second IOL device 202B to modify the focal length of the lens 116 responsive to the determined apparent object distance.

Figure 2B:
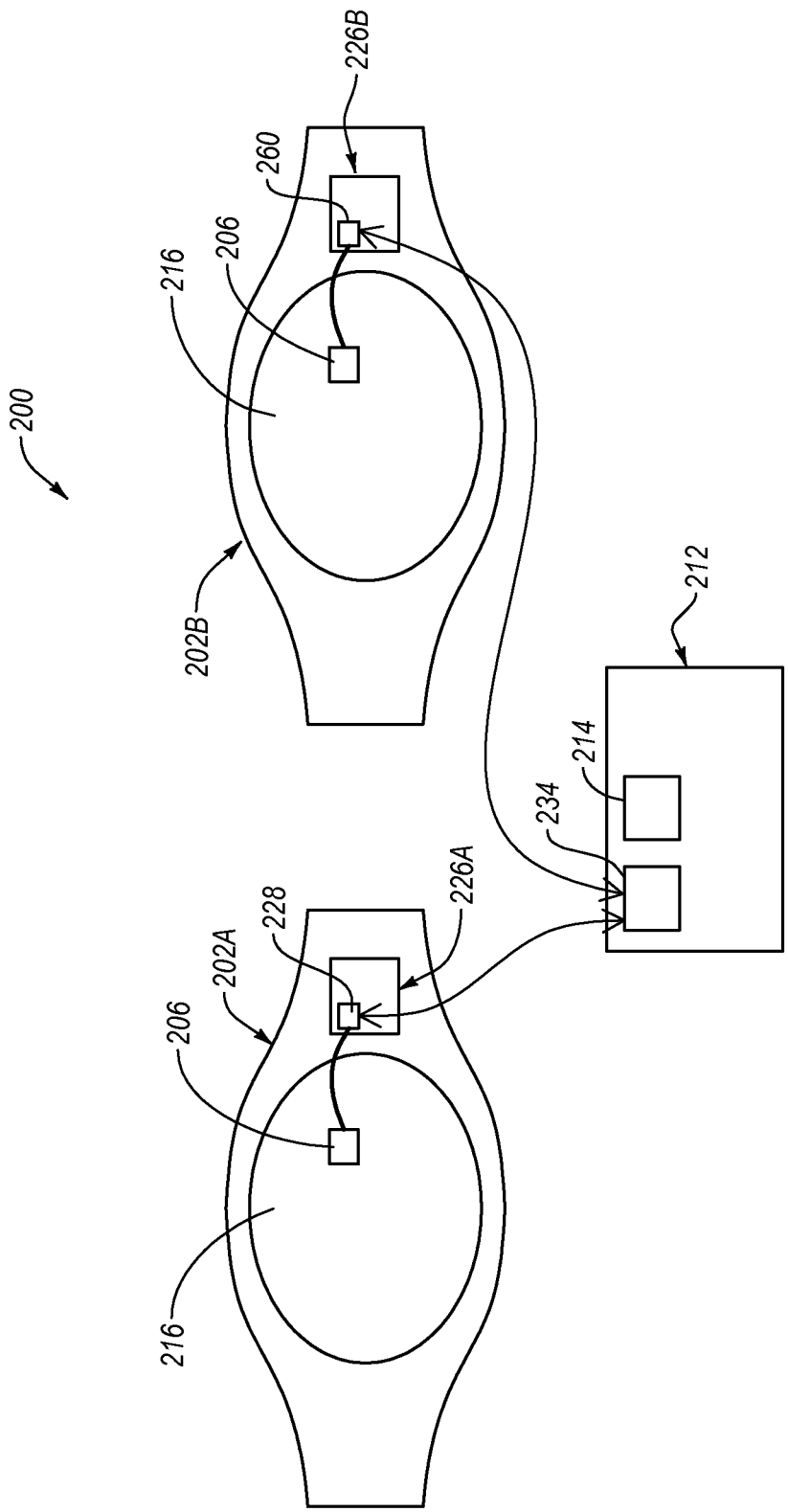
FIG. 2B is a schematic illustration of a portion of an IOL system, according to an embodiment.

FIG. 2B is a schematic illustration of a portion of the IOL system 200, according to an embodiment. The first IOL device 202A includes one or more portions 226A configured to have one or more components of the IOL system 200 positioned therein. For example, the one or more portions 226A of the first IOL device 202A can include a first communication device 228. The first communication device 228 can be configured to transmit one or more communication signals to the controller 212. The one or more communication signals can include or encode at least a portion of the one or more detection signals. As such, the first communication device 228 can be operably or communicatively coupled to the one or more photodetectors 206. The first communication device 228 can be configured to receive one or more control signals from the controller 212. The one or more control signals can include at least one direction from the control electrical circuitry 214, such as directions to change the focal length of the lens 216.

The second IOL device 202B is substantially similar to or the same as the first IOL device 202A. For example, the second IOL device 202B includes one or more portions 226B. The one or more portions 226B of the second IOL device 202B includes a third communication device 260. The third communication device 260 can be configured to transmit one or more communication signals to the controller 212. The third communication device 260 can also receive one or more control signals from the controller 212.

In an embodiment, the first communication device 228 and the third communication device 260 are configured to communicate with each other. For example, the first communication device 228 can transmit one or more communication signals to the third communication device 260. The third communication device 260 can then relay or transmit such one or more communication signals to the second communication device 234.

The controller 212 can be substantially similar to the controller 112 shown in FIG. 1A. For example, the controller 212 includes a second communication device 234 configured to receive the one or more communication signals from the first communication device 228 or the third communication device 260. The second communication device 234 can also transmit one or more control signals to the first communication device 228 or the third communication device 260. In an embodiment, the second communication device 234 can transmit one or more control signals that are substantially the same to both the first communication device 228 and the third communication device 260. In an embodiment, the second communication device 234 can transmitted one or more control directives to the first communication device 228 that are substantially different from one or more control signals transmitted to the third communication device 260. For example, the second communication device 234 can transmit a first control signal to the first communication device 228 containing directions to change the focal length of the lens 216 of the first IOL device 202A. The second communication device 234 can also transmit a second control signal to the third communication device 260 containing directions to not change the focal length of the lens 216 of the second IOL device 202B.

The control electrical circuitry 214 can determine the presence of the object or the apparent object distance. In an embodiment, the control electrical circuitry 214 can determine the presence of the object or the apparent object distance using substantially the same methods described in FIGS. 1A, 1D, and 1E. In an embodiment, the control electrical circuitry 214 can compare the angular position of the light 208 detected by the one or more photodetectors 206 of the first IOL device 202A and the angular position of the light 208 detected by the one or more photodetectors 206 of the second IOL device 202B to determine a vergence rotation between the first eye 204A and the second eye 204B. The control electrical circuitry 214 can use the vergence rotation between the first eye 204A and the second eye 204B to determine the apparent object distance.

Figure 3A:
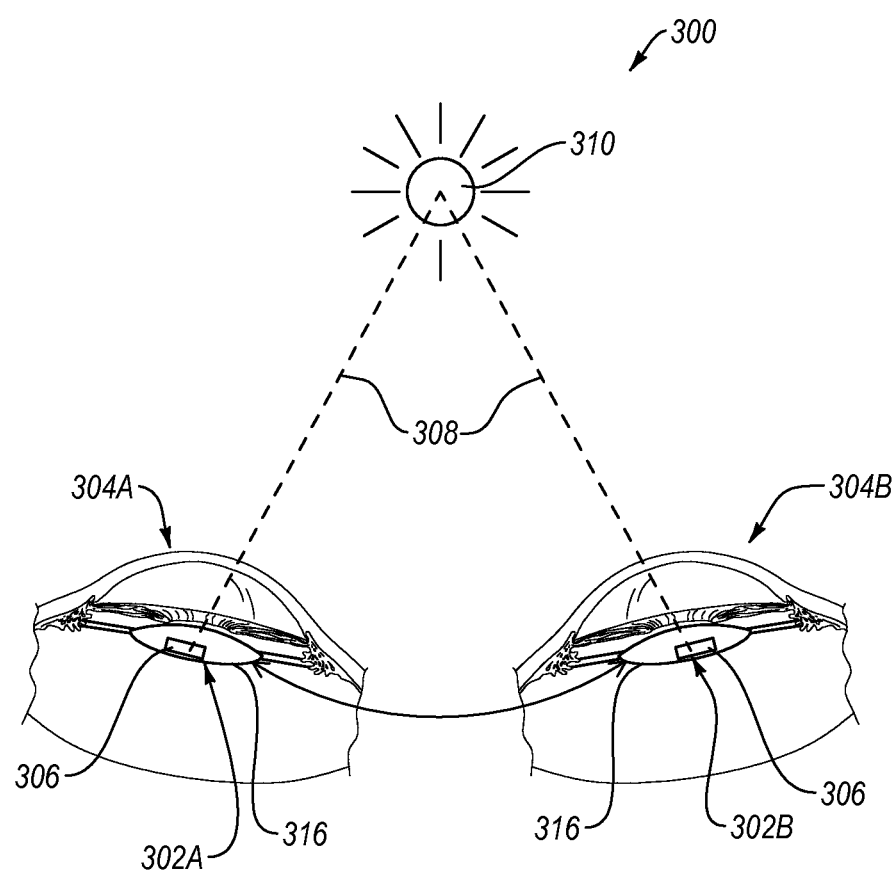
FIG. 3A is a schematic illustration of an IOL system, according to an embodiment.

FIG. 3A is a schematic illustration of an IOL system 300, according to an embodiment. The IOL system 300 is substantially similar to or the same the IOL system 200 shown in FIG. 2A. For example, the IOL system 300 includes a first IOL device 302A and a second IOL device 302B. The first IOL device 302A is implanted in a first eye 304A of the subject and the second IOL device 302B is implanted in a second eye 304B of the subject. The first IOL device 302A and the second IOL device 302B can each include one or more photodetectors 306 and a lens 316 having a modifiable focal length. For example, the lens 316 can be configured as any of the lenses disclosed herein. The one or more photodetectors 306 are configured to detect a light 308 emitted by a light source 310.

Figure 3B:
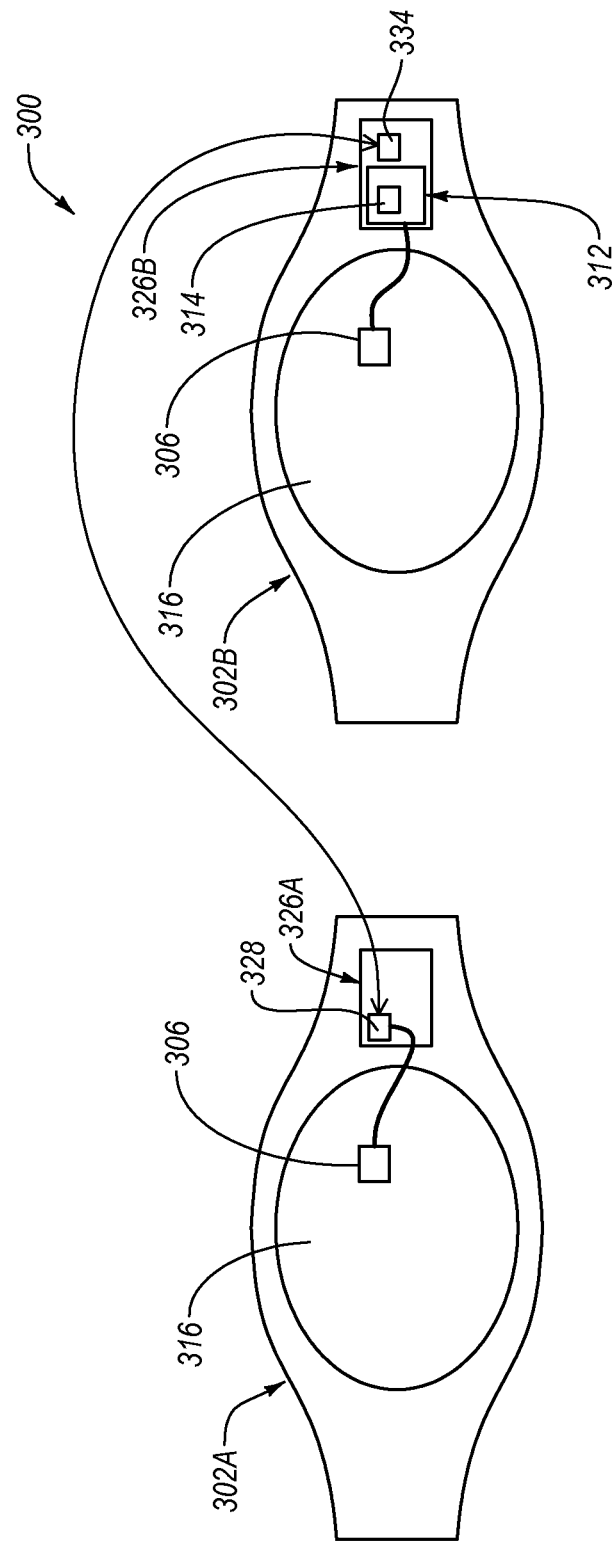
FIG. 3B is a schematic illustration of a portion of an IOL system, according to an embodiment.

FIG. 3B is a schematic illustration of a portion of the IOL system 300, according to an embodiment. The first IOL device 302A includes one or more portions 326A configured to have one or more components of the IOL system 300 positioned therein. The one or more portions 326A of the first IOL device 302A can include a first communication device 328 configured to transmit one or more communication signals to a second communication device 334. The one or more communication signals can include one or more detections signals outputted by the one or more photodetectors 306 or information about the one or more detection signals when the one or more photodetectors 306 detect the light 308.

The second IOL device 302B includes one or more portions 326B configured to having one or more components of the IOL system 300 positioned therein. The one or more portions 326B of the second IOL device 302B includes the controller 312 positioned therein. The controller 312 includes the control electrical circuitry 314. The one or more portions 326B also include a second communication device 334. The second communication device 334 can be integral with the controller 312 or can be distinct and separate from the controller 312. The second communication device 334 can be configured to receive the one or more communication signals from the first communication device 328. The second communication device 334 can transmit the one or more communication signals or portions of the one or more communication signals to the controller 312 or the control electrical circuitry 314. In an embodiment, the one or more photodetectors 306 of the second IOL device 302B can output one or more detection signals to the control electrical circuitry 314. For example, the one or more photodetectors 306 outputs the one or more detection signals to the second communication device 334 that then relays the one or more detection signals to the controller 312 or the control electrical circuitry 314. Alternatively, the one or more photodetectors 306 outputs the one or more detection signals to the controller 312 or the control electrical circuitry 314. The control electrical circuitry 314 can then determine the presence of the object or the apparent object distance using the one or more detection signals from the first IOL device 202A or the second IOL device 202B.

Figure 4A:
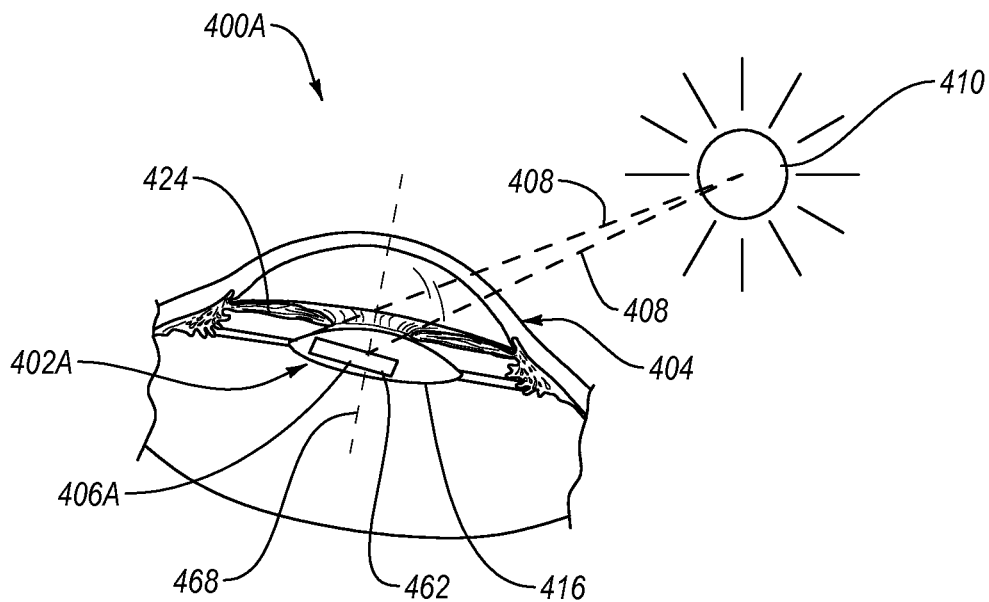
FIGS. 4A and 4B are schematic side, cross-sectional views of IOL systems utilizing different photodetectors, according to an embodiment.
Figure 4B:
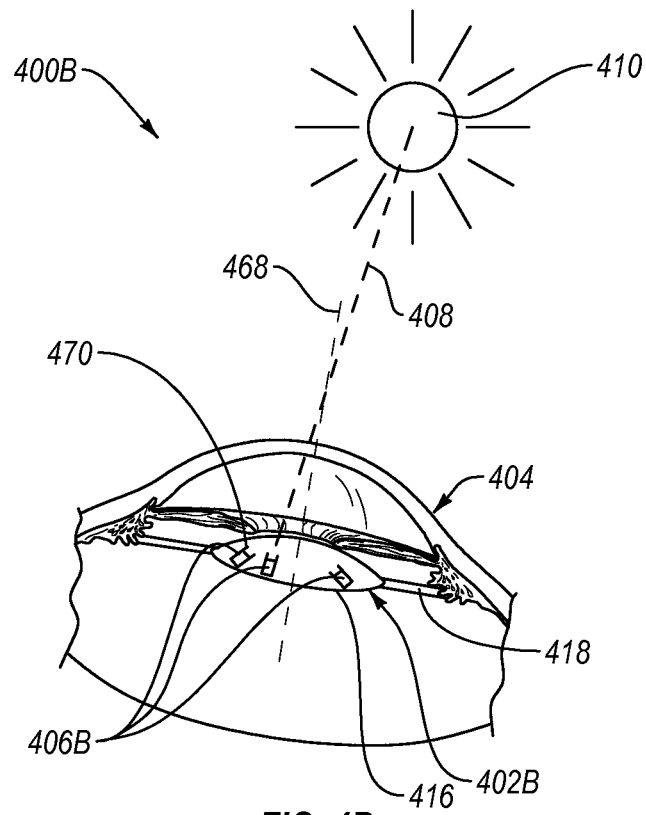

FIGS. 4A and 4B are schematic side, cross-sectional views of IOL systems utilizing different photodetectors, according to an embodiment. The different photodetectors can be used with any of the embodiments illustrated and described in connection with the IOL systems 100, 200, and 300 shown in FIGS. 1A to 3B. Although only a single type of photodetector is shown in FIGS. 4A and 4B, it should be understood that the IOL systems incorporating the photodetectors shown in FIGS. 4A and 4B can include a plurality of different types of photodetectors disclosed herein.

FIG. 4A illustrates an IOL system 400A including at least one IOL device 402A that is implanted in at least one eye 404 of a subject. The IOL device 402A includes a lens 416 that exhibits a modifiable focal length. For example, the lens 416 can be configured as any of the lenses disclosed herein. The IOL system 400A includes one or more photodetectors 406A configured to detect light 408. In an embodiment, the light 408 can be emitted by a light source 410. The one or more photodetectors 406A can output one or more detection signals responsive to detecting the light. The IOL system 400A can use the one or more detection signals to determine an apparent object distance. The IOL system 400A can change the focal length of the lens 416 responsive to the one or more detection signals and according to the apparent object distance.

The one or more photodetectors 406A can include an array 462 having a plurality of photodetectors that are arranged an array. For example, the array 462 can be a two-dimensional structure (e.g., a flat surface) or a three-dimensional structure (e.g., a curved surface). In an embodiment, the array 462 can exhibit a generally circular cross-sectional geometry, a generally rectangular cross-sectional geometry, or any suitable cross-sectional geometry. In an embodiment, the plurality of photodetectors can include a plurality of pixel sensors. For example, the array 462 can include an active-pixel array or a flat panel detector. In an embodiment, the array 462 can include a plurality of photodiodes or other photodetectors arranged in a selected pattern. In an embodiment, the array 462 can be configured to detect the light 408 at a plurality of angular positions relative to the array 462.

The array 462 can be positioned in the IOL device 402A such that light 408 can be partially occluded from reaching portions of the array 462. The light can be at least partially occluded by an item that has a known position relative to the array 462. In the illustrated embodiment, the array 462 is positioned in the IOL device 402A such that, at certain angles, the iris 424 prevents the light 408 from reaching the entire array 462. As such, when the light 408 is partially occluded, the array 462 can include a first portion that detects the light 408 and a second portion that does not detect the light 408. In an embodiment, the angular position of the light 408 can be determined by analyzing which portions of the array 462 detect the light 408 and which portions of the array 462 do not detect the light 408. In an embodiment, the array 462 can be configured to detect the position of the inner most edge of the iris 424 because the inner most edge of the iris 424 can move relative to the array 462. The light 408 can also be at least partially occluded by one or more components of the IOL system 400A. For example, the IOL system 400A can include a controller (not shown) configured to at least partially occlude the light 408. In other embodiments, the light 408 can be at least partially occluded by other items, such as the nose of the subject, eyelashes of the subject, additional structures in the eye 404 (e.g., blood vessels), etc.

In an embodiment, the array 462 can be at least partially positioned at, in, or along a visual axis (not shown) of the eye 404. The visual axis draws a line from the center of the pupil to the fovea of the retina. For example, the array 462 can be placed at or near the pupil. In an embodiment, the array can be at least partially positioned at, in, or along an optical axis 468 of the eye 404. In either embodiment, the array 462 can be configured to not substantially interfere with or obstruct the vision of the subject. For example, the array 462 can exhibit a shape that enables the array 462 to be substantially out of focus at the retina 620. For example, the array 462 can exhibit a cross-sectional geometry that is relatively wide in one direction but relatively narrow in another direction. In an embodiment, the entire array 462 or at least one component of the array 462 can be substantially small (e.g., an array 462 of small sensors). In an embodiment, at least one component of the array 462 can be at least partially transparent to visible light.

In an embodiment, any of the one or more photodetectors disclosed herein (e.g., the one or more photodetectors 106 shown in FIG. 1A, the one or more photodetectors 206 shown in FIG. 2A, the one or more photodetectors 306 shown in FIG. 3A) can be at least partially positioned at, in, or along the visual axis or optical axis 468 of the eye 404. Any of the sensors at least partially positioned at, in, or along the visual axis can also be configured to not substantially interfere with or obstruct the vision of the subject. For example, any of the sensors can exhibit a shape, size, or transparency that does not substantially interfere with or obstruct the vision.

FIG. 4B illustrates an IOL system 400B including at least one IOL device 402B that is implanted in at least one eye 404 of a subject. The IOL device 402B includes a lens 416 that exhibits a modifiable focal length. The IOL system 400B also includes one or more photodetectors 406B configured to detect light 408. In an embodiment, the light 408 can be emitted by the light source 410. The one or more photodetectors 406B can output one or more detection signals responsive to detecting the light 408. The IOL system 400B can use the one or more detection signals to determine the apparent object distance. The IOL system 400B can change the focal length of the lens 416 responsive to the one or more detection signals and according to the determined position of the object.

In the illustrated embodiment, the one or more photodetectors 406B include a plurality of photodetectors 406B. In an embodiment, each of the plurality of photodetectors 406B is configured to detect the light 408 at a specific angular direction or specific angular range relative to the photodetector 406B. For example, in the illustrated embodiment, each of the plurality of photodetectors 406B includes a blinder 470 configured to limit the angular range that each photodetector 406B can detect the light 408. In an embodiment (not illustrated) each of the plurality of photodetectors 406B is coupled to a separate optical waveguide (e.g., an optical fiber) having a limited optical acceptance angle. In this embodiment, each optical waveguide can be separately oriented, such that each will only accept light from a unique direction and, hence, each of the coupled photodetectors is only responsive to light from a specific direction relative to the IOL, and hence relative to the respective eye. In an embodiment, each of the plurality of photodetectors 406B is configured of detect the light 408 at a different angular direction or angular range than another photodetector 406B. For example, only one or some of the illustrated photodetectors 406B can detect the light 408 emanating from a location at a specific angular direction or angular range.

In an embodiment, each of the plurality of photodetectors 406B can detect the light 408 at a specific angular range and the specific angular range detected by each photodetector 406B can at least partially overlap a specific angular range detected by another photodetector 406B. For example, the plurality of photodetectors 406B can include a first photodetector and a second photodetector. The first photodetector can be configured to detect light at a first angular range and the second photodetector can be configured to detect light at a second angular range. The first angular range and the second angular range can at least partially overlap to form an overlapped range. If only the first or second photodetector detects the light, the control electrical circuitry (not shown) knows that the angular range of the light is within the first or second angular range, respectively, minus the portions of the first or second angular range that includes the overlapped range. However, if both the first and second photodetectors detects the light, the control electrical circuitry knows that the angular range of the light is within the overlapped range and, in one or more embodiments, the control electrical circuitry can controllably change the focal length the lens 416 responsive to the first and second photodetectors indicating the light being in the overlapped angular range and vergence of the eyes being detected.

In an embodiment, each of the plurality of photodetectors 406B can be embodied as two or more partially overlapping layers of photodetectors. For example, the two or more partially overlapping layers of photodetectors can include two or more partially overlapping thin film photodetectors (e.g., partially overlapping thin film photodiodes made from silicon photodiodes, gallium arsenide photodiodes, other elemental or compound semiconductor photodiodes, or other photoactive compounds or layers). In an embodiment, the two or more partially overlapping layers of photodetectors can be made from semiconductor quantum dots, such as CdSe or CdTe encapsulated with zinc sulfide (ZnS), with the ZnS coated with one or more types of hydrophillic or amphiphillic molecules. A first one of the two or more partially overlapping layers of photodetectors can be positioned and configured to detect light at a first angular range and at least a second one of the two or more partially overlapping layers of photodetectors can be positioned configured to detect light at a second angular range. The first angular range and the second angular range can at least partially overlap to form an overlapped range. If only the first one or second one of the two or more partially overlapping layers of photodetectors detects the light, the control electrical circuitry (not shown) knows that the angular range of the light is within the first or second angular range, respectively, minus the portions of the first or second angular range that includes the overlapped range. However, if both the first one and second one of the two or more partially overlapping layers of photodetectors detect the light, the control electrical circuitry knows that the angular range of the light is within the overlapped range because an electrical signal generated by the two or more partially overlapping photodetectors is relatively stronger and, in one or more embodiments, the control electrical circuitry can controllably change the focal length the lens 416 responsive to the first one and second one of the two or more partially overlapping layers of photodetectors indicating the light being in the overlapped angular range and vergence of the eyes being detected.

The plurality of photodetectors 406B can be positioned in the lens 416, can coat or cover a portion of the lens 416 when the plurality of photodetectors 406B are embodied as partially overlapping layers of photodetectors, or can be positioned in another portion of the IOL system 400A that can receive the light 408 (e.g., the haptic 418). In the illustrated embodiment, the plurality of photodetectors 406B are spaced from the optical axis 468. However, in other embodiments, at least one of the plurality of photodetectors 406B can be at least partially positioned within the optical axis 468. In an embodiment when the plurality of photodetectors 406B are embodied as partially overlapping layers of photodetectors, the photodetectors 406B can be at least partially optically transparent or sufficiently small so as to not interfere with the subject's vision.

Figure 5:
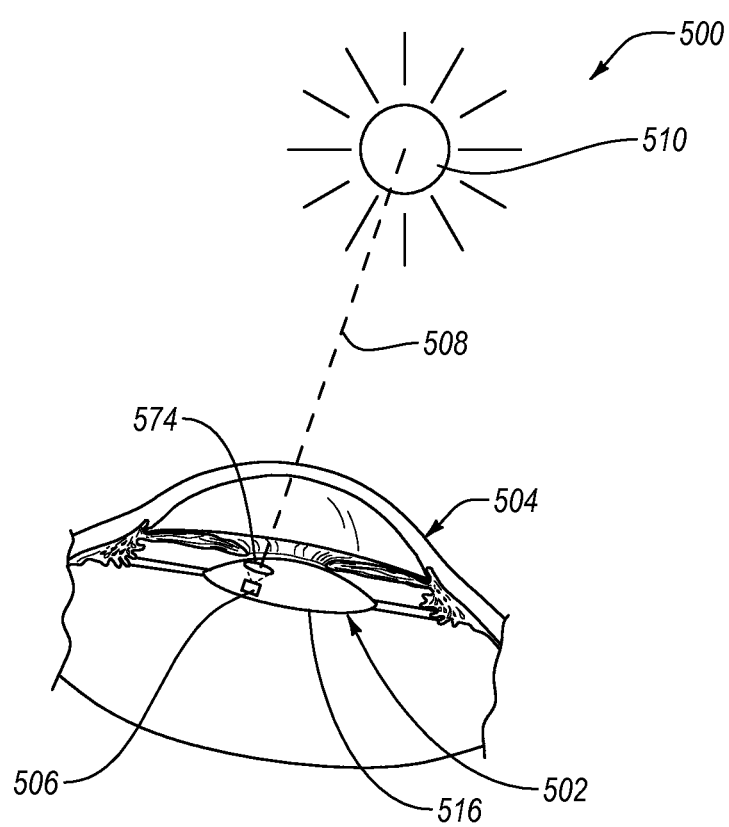
FIG. 5 is a schematic illustration of an IOL system including at least one optical element, according to an embodiment.

FIG. 5 is a schematic illustration of an IOL system 500 that include at least one optical element 572, according to an embodiment. The IOL system 500 includes at least one IOL device 502 that is implanted in an eye 504 of a subject. The IOL device 502 includes a lens 516 that has a modifiable focal length. The IOL system 500 further one or more photodetectors 506 configured to detect light 508. In an embodiment, the light 508 can be emitted by a light source 510. The one or more photodetectors 506 output one or more detection signals responsive to detecting the light 508. The IOL system 500 can determine the presence of the object or apparent object distance using the one or more detection signals.

The IOL system 500 further includes at least one optical element 572. The at least one optical element 572 can be configured to receive the light 508 and direct the light 508 towards the one or more photodetectors 506. In an embodiment, the optical element 572 can be configured to only direct the light 508 towards the one or more photodetectors 506 when the at least one optical element 572 receives the light 508 at a selected angular position or angular range. In the illustrated embodiment, the at least one optical element 572 includes a focusing lens 574. The focusing lens 574 can be configured to receive light 508 and focus the light towards the one or more photodetectors 506. The focusing lens 574 can be configured to uniquely coordinate direction of the light 508 to location of the one or more photodetectors 506.

The at least one optical element 572 can include additional components configured to direct the light 508 towards the one or more photodetectors 506. In an embodiment, the at least one optical element 572 can include a prism. In such an embodiment, the prism can refract the received light towards the one or more photodetectors 506. Additionally, the prism can separate the light 508 from the background light. In an embodiment, the at least one optical element 572 can include any of the previously discussed filters. In an embodiment, the at least one optical element 572 can include a surface configured to reflect or diffract the light 508 towards the one or more photodetectors 506 (e.g., a reflecting or diffractive surface).

It should be noted that other optical elements can be employed besides a focusing lens. Additionally, as previously noted, the at least one optical element 572 can be used with any of the embodiments illustrated and described in connection with any of the IOL systems disclosed herein.

Figure 6A:
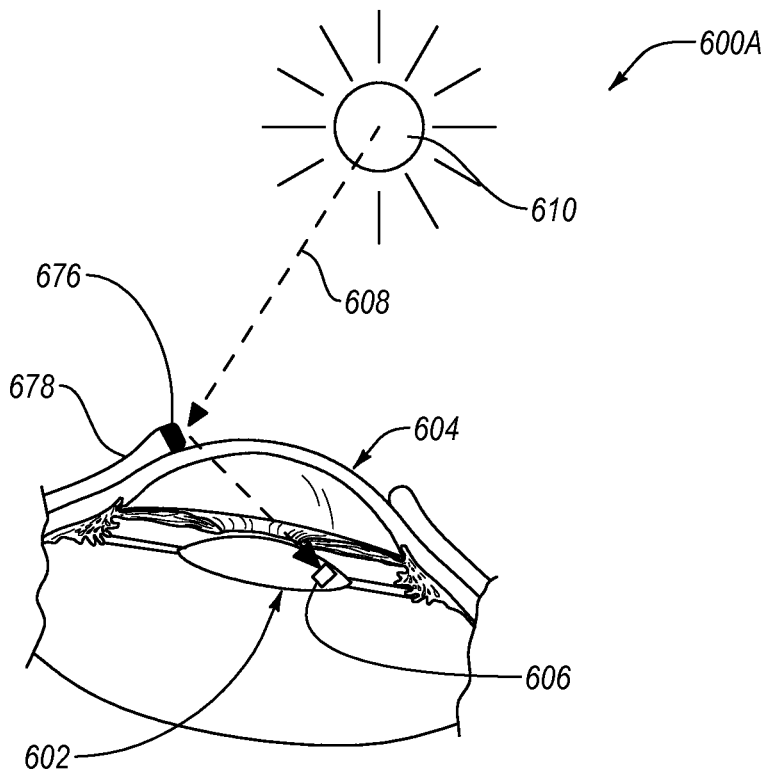
FIGS. 6A and 6B are schematic illustrations of an IOL system including at least one reflector positioned externally from an IOL, according to an embodiment.
Figure 6B:
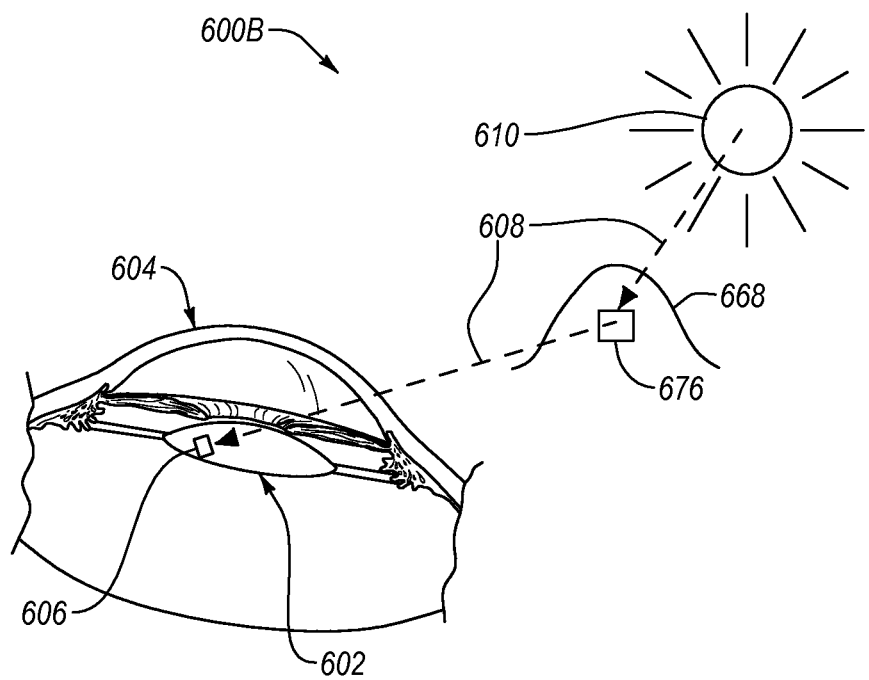

FIGS. 6A and 6B are schematic illustrations of IOL systems including at least one light reflector 676 positioned externally from an IOL configured to reflect light. The at least one light reflector 676 can be used with any of the IOL system embodiments illustrated and described herein.

FIG. 6A illustrates an IOL system 600A, according to an embodiment. The IOL system 600A includes at least one IOL device 602 implanted in an eye 604 of a subject. The IOL system 600A further includes one or more photodetectors 606 configured to detect light 608. In an embodiment, the light 608 can be emitted by a light source 610. The one or more photodetectors 606 can output one or more detection signals responsive to detecting the light 608. The IOL system 600A can determine the presence of the object or the apparent object distance using the one or more detection signals and modify a focal length of a lens of the at least one IOL device 602 responsive to the one or more photodetectors 606 sensing the light 608.

The IOL system 600A further includes at least one light reflector 676. The at least one light reflector 676 can include a reflecting surface (e.g., a plurality of reflecting surfaces) configured to reflect the light 608. In an embodiment, the reflecting surface of the at least one light reflector 676 can include an optical reflector (e.g., a plane mirror, a curved mirror), a diffractive surface (e.g., a diffraction grating), or an optical scatterer (e.g., multi-faceted mirror). In an embodiment, the reflecting surface of the at least one light reflector 676 includes an active mirror or a non-reversing mirror. In an embodiment, the reflecting surface of the at least one light reflector 676 is configured to reflect only certain wavelengths of light. As such, the reflecting surface of the at least one light reflector 676 can filter the light that reaches the one or more photodetectors 606. For example, the reflecting surface of the at least one light reflector 676 can include a dielectric mirror (e.g., a hot mirror, a cold mirror), or a metallic mirror that is selectively reflective to light having a specific wavelength or range of wavelengths.

In an embodiment, the at least one light reflector 676 can have a known location relative to the one or more photodetectors 606. Additionally, the reflecting surface can have a known orientation relative to at least one component of the IOL system 600A. For example, in the illustrated embodiment, the at least one light reflector 676 is sized and configured to be mounted to the eyelid 678 of the subject. However, the eyelid 678 can move and change its position relative to the one or more photodetectors 606. As such, in an embodiment, the one or more photodetectors 606 can be configured to determine the position of the at least one light reflector 676 relative to the one or more photodetectors 606. In an embodiment, the at least one light reflector 676 can be positioned such that the at least one light reflector 676 only reflects the light 608 towards the one or more photodetectors 606 when the eyelid 678 has a certain position or range of positions relative to the one or more photodetectors 606.

FIG. 6B illustrates an IOL system 600B. The IOL system 600B can be substantially similar to the IOL system 600B shown in FIG. 6A. For example, the IOL system 600B can include an IOL device 602 that is implanted in an eye 604 of a subject. The IOL system 600B further includes one or more photodetectors 606 configured to detect the light 608. The light 608 can be emitted by a light source 610. The one or more photodetectors 606 can output one or more detection signals responsive to detecting the light 608. The IOL system 600B can determine the apparent object distance using the one or more detection signals and modify a focal length of a lens of the at least one IOL device 602 responsive to the one or more photodetectors 606 sensing the light 608.

The IOL system 600B further includes at least one light reflector 676. The at least one light reflector 676 can be substantially similar to the at least one light reflector 676 shown in FIG. 6A. However, in the illustrated embodiment, the at least one light reflector 676 sized and configured to be mounted on the nose 680 of the subject. The at least one light reflector 676 can be positioned on the nose 680 such that the at least one light reflector 676 reflects light towards the one or more photodetectors 606. In an embodiment, the IOL system 600B is configured to determine the presence of the object or the position of the at least one light reflector 676 relative to the one or more photodetectors 606 since the nose 680 can slightly move. However, in other embodiments, the IOL system 600B can be configured to not determine the position of the at least one light reflector 676.

In other embodiments, the at least one light reflector 676 can be sized and configure to be mounted on different body parts on the subject. For example, the at least one light reflector 676 can be size and configured to be mounted on an eyelash, a finger, a hand, an arm, or any other suitable body part of the subject. In an embodiment, the at least one light reflector 676 can be sized and configured to be mounted on an article worn by the subject. For example, the at least one light reflector 676 can be sized and configured to be mounted on a ring, a bracelet, eyeglasses, a shirt, a watch, a wristband, or any other suitable article worn by the subject. In any of the foregoing embodiments, the IOL system 600B can be configured to determine the relative position of the at least one light reflector 676 relative to the one or more photodetectors 606.

Figure 7A:
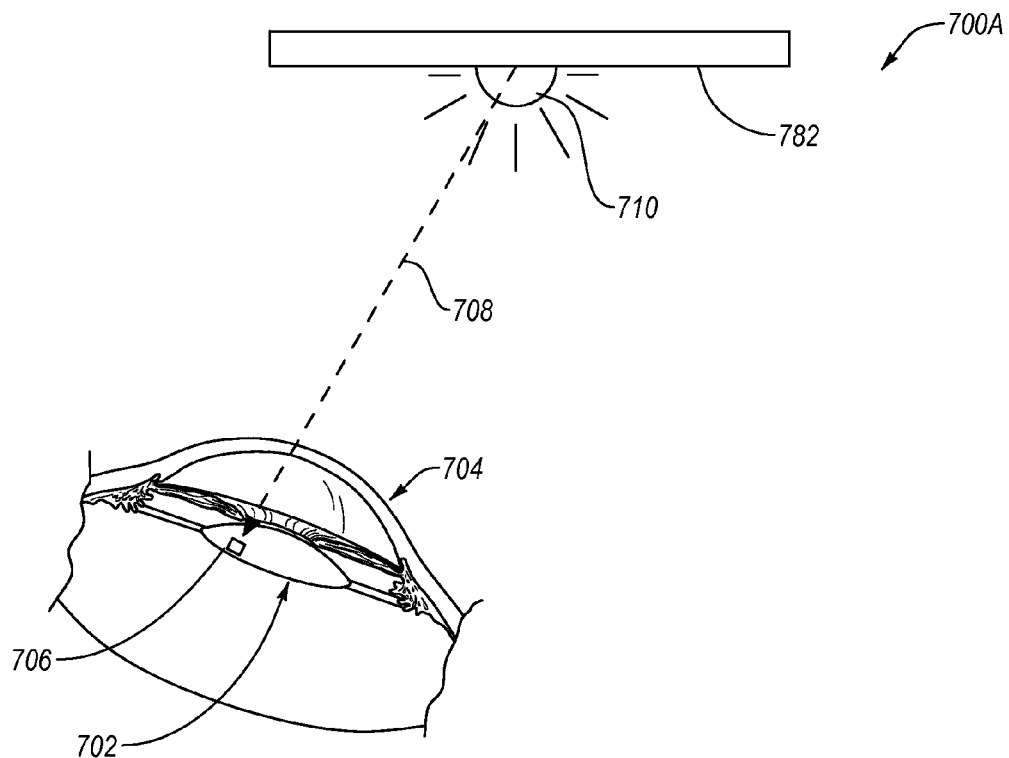
FIG. 7A is a schematic illustration of an IOL system, according to an embodiment.

FIG. 7A is a schematic illustration of an IOL system 700A, according to an embodiment. The IOL system 700A includes an object 782. The object 782 can be any object that a subject looks at, such as a laptop, a monitor such as a monitor of a desktop computer, or an e-reader, etc. In an embodiment, the IOL system 700A can be configured to determine the apparent object distance of the object 782 from the subject or modify a focal length of a lens of the IOL system 700A responsive to receiving an indication that the subject is near the object 782.

The IOL system 700A includes a light source 710 configured to emit light 708. The light source 710 can be mounted on object 782, or can be mounted elsewhere (e.g., on a wall, on furniture, on a ceiling, etc.) such that while the subject is actively looking at object 782, light source 710 is also within his field of view. The light 708 can be configured to be distinguishable from background light. For example, the light source 710 can emit the light 708 at a selected wavelength, amplitude, or polarization, or the light source 710 can emit pulses of the light 708 having a selected frequency, a selected pattern, or a predictive pattern. The IOL system 700A includes one or more photodetectors 706 configured to detect the light 708. The one or more photodetectors 706 outputs one or more detection signals responsive to detecting the light 708.

The IOL system 700A can determine the position of the light source 710 relative to a component of the IOL system 700A or the IOL system 700A can modify a focal length of a lens of the IOL system 700A responsive to receiving an indication that the subject is near the object 782. For example, the light 708 can enable the IOL system 700A to determine the apparent object distance. For example, the light source 710 can have a known position relative to the object 782. In an embodiment, the light source 710 is positioned on or near the object 782. In an embodiment, the exact position of the light source 710 on the object 782 is known. In an embodiment, the light source 710 can be spaced from the object 782. However, the light source 710 can have a known position relative to the object 782. Therefore, determining the position of the light source 710 relative to one or more photodetectors 706, the IOL 702, or the eye 704 enables the IOL system 700A to determine the apparent object distance. In an embodiment, the IOL system 700A can modify a focal length of a lens of the IOL system 700A responsive to receiving an indication that the subject is near the object 782 which can be responsive to the one or more photodetectors 706 receiving the light 708 having any of the above selected characteristics, such as a selected wavelength, a selected amplitude, a selected polarization, a selected pulse pattern having a selected frequency, a selected pattern, or a predictive pattern. For another example, the light source 710 need not have a known position relative to the object 782. Determining the angle of light 708 reaching each eye from light source 710 can be used to determine a vergence angle between the two eyes, and hence an eye convergence distance to object 782.

Figure 7B:
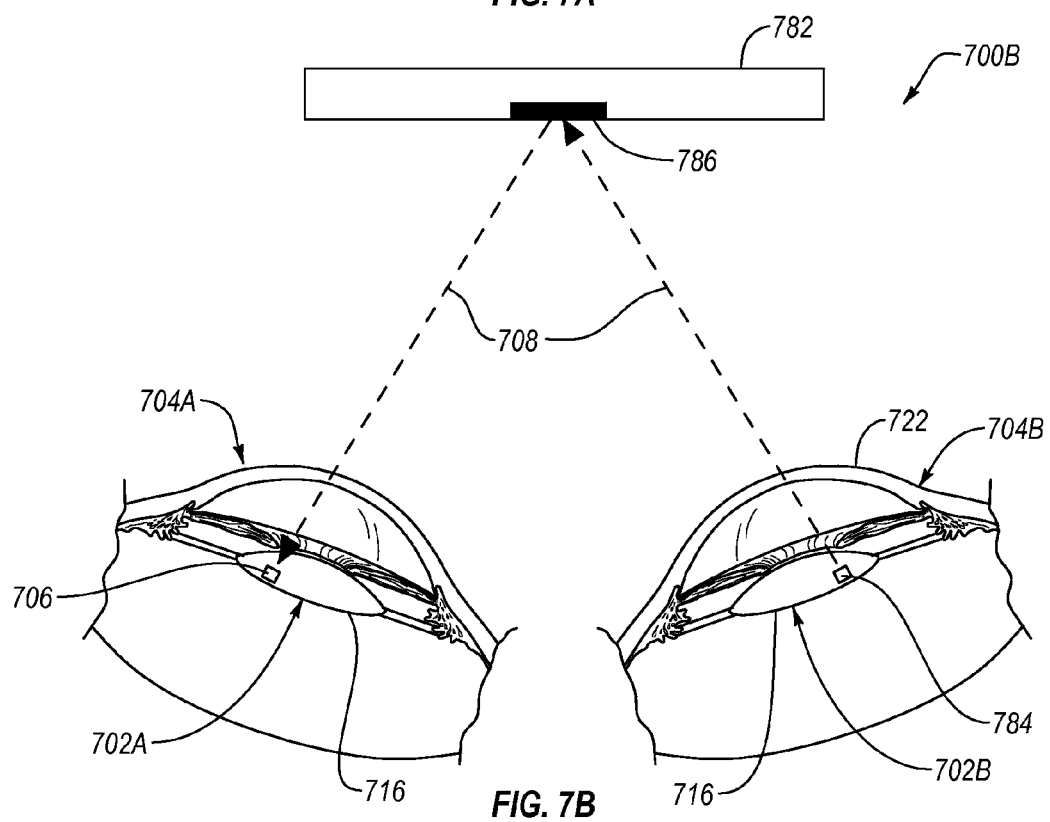
FIG. 7B is a schematic illustration of an IOL system, according to an embodiment.

FIG. 7B is a schematic illustration of an IOL system 700B according to an embodiment. The IOL system 700B includes a first IOL device 702A implanted in a first eye 704A of the subject and a second IOL device 702B implanted in a second eye 704B of the subject. In an embodiment, the second IOL device 702B can include a light source positioned in or near the second IOL device 702B. For example, the second IOL device 702B can include an embedded light source 784 therein. The embedded light source 784 can be any light source configured to emit a light 708 (e.g., an LED, a laser, etc.) having a suitable size to be positioned in the second IOL 702B. The embedded light source 784 can emit the light 708 through a cornea 722 of the second eye 704B towards an exterior surface. In an embodiment, the embedded light source 784 can be configured to emit the light 708 at an known angle relative to the second IOL 702B (e.g., using a laser) or can be configured to emit the light 708 at a range of angles (e.g., using an LED). In an embodiment, the embedded light source 784 can be configured to emit a light having certain characteristics (e.g., a selected wavelength, amplitude, or polarization). In an embodiment, the embedded light source 784 can be configured to emit the light 708 in pulses having a selected frequency, a selected pattern, or a selected predictive pattern.

The IOL system 700B can also include a reflector 786 configured to reflect the light 708 emitted by the embedded light source 784. The reflector 786 can include any of the reflecting surfaces or structures disclosed herein. In an embodiment, the reflector 786 can have a known position relative to the object 782. For example, the reflector 786 can be positioned on the object 782 or be positioned remotely from the object 782.

The first IOL 702A can include one or more photodetectors 706 positioned therein. The one or more photodetectors 706 can be configured to detect the light 708 emitted by the embedded light source 784 and reflected by the at least one reflector 786. The one or more photodetectors 706 can output one or more detection signals responsive to detecting the light 708. The IOL system 700B can determine the apparent object distance using the one or more detection signals. For example, the IOL system 700B can determine the angular position of the at least one reflector 786 relative to the one or more photodetectors 706. The IOL system 700B can then use additional information, such as the distance between the one or more photodetectors 706 and the embedded light source 784 to determine apparent object distance. In an embodiment, the second IOL 702B can also include one or more photodetectors 706, which (like the ones in IOL 702A) can output one or more detection signals responsive to detecting the light 708. The IOL system 700B can then determine the apparent object distance by comparing detection signals from photodetectors in both IOL 702A and 702B. For example, the IOL system 700B can determine the angular position of the at least one reflector 786 relative to each eye, thereby determining a vergence between the two eyes. The first and second IOL devices 702A and 702B, respectively, can each include a lens 716 exhibiting a modifiable focal length. The first and second IOL devices 702A and 702B, respectively, can change the focal length their respective lens 716 responsive to the apparent object distance determined by the IOL system 700B.

In an embodiment, the second IOL 702B and the first IOL 702A can be configured to communicate with each other. For example, each of the first IOL device 702A and the second IOL device 702B can include respective communication devices (not shown) that enable the second IOL device 702B to communicate to the first IOL 702A and vice versa. In an embodiment, the second IOL device 702B can communicate to the first IOL device 702A when the embedded light source 784 emits the light 708, the characteristics of the light 708, or the frequency at which the light 708 is emitted. In an embodiment, the first IOL 702A can communicate the apparent object distance to the second IOL 702B.

It should be noted that in other embodiments, different types of sensors in addition to or alternatively to photodetectors can be used for sensing feedback in an IOL system. For example, one or more sensors can be chosen from at least one of one or more accelerometers, one or more gyroscopes, one or more magnetic field sensors, or one or more photodetectors. For example, suitable magnetic field sensors used in conjunction with suitable magnetic field sources is disclosed in U.S. patent application Ser. No. 14/807,719 to Roderick A. Hyde, et al. titled "Intraocular Lens Devices, Systems, and Related Methods" and filed concurrently herewith, the disclosure of which is incorporated herein by this reference, in its entirety.

In an embodiment, an IOL system includes a first IOL device configured to be implanted in a first eye of a subject. The first IOL device includes a first IOL exhibiting a selectable or modifiable focal length. The first IOL device includes one or more first sensors configured to determine information associated with an angular orientation of the first eye and output one or more first orientation signals responsive to the information. For example, the one or more first sensors can be chosen from at least one of one or more accelerometers, one or more gyroscopes, one or more magnetic field sensors, or one or more photodetectors. The first IOL device further includes a first communication device. The IOL system also includes a second IOL device configured to be implanted in a second eye of the subject. The second IOL device includes a second IOL exhibiting a selectable or modifiable focal length. The second IOL device includes one or more second sensors configured to determine information associated with an angular orientation of the second eye and output one or more second orientation signals responsive the information. For example, the one or more second sensors can be chosen from at least one of one or more accelerometers, one or more gyroscopes, one or more magnetic field sensors, or one or more photodetectors. The second IOL device further includes a second communication device configured to operably couple the second communication device to the first communication device.

The IOL system additionally includes a controller operably coupled to each of the first IOL device and the second IOL device. The controller can be positioned in the first or second IOL device, or located externally such as being carried or worn by the subject. The controller is configured to receive the one or more first orientation signals from the one or more first sensors of the first IOL device and the one or more second detection signals from the one or more second sensors of the second IOL device. The controller includes electrical circuitry configured to direct each of the first IOL device and the second IOL device to controllably modify the modifiable focal length of the respective IOLs thereof responsive to the one or more first orientation signals and the one or more second orientation signals.

The controller is configured to determine a focal length modification for the first intraocular lens or the second intraocular lens based on comparing the first orientation signal with the second orientation signal in order to determine a vergence angle between the first eye and the second eye. In an embodiment, the controller is configured to determine a focal length modification for the first intraocular lens or the second intraocular lens based on comparing the first orientation signal with the second orientation signal in order to distinguish between a vergence angle between the first eye and the second eye from a co-tilt angle common to both the first eye and the second eye It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A method, comprising:
    at one or more of a first eye or a second eye of a subject, receiving incident light entering the first eye or the second eye, wherein the first eye includes a first intraocular lens device and the second eye includes a second intraocular lens device, each of the first intraocular lens device and the second intraocular lens device including one or more photodetectors and an intraocular lens exhibiting a modifiable focal length;
    with the one or more photodetectors, detecting the incident light and outputting one or more detection signals responsive to the detecting;
    with a controller, determining a direction of the incident light relative to the first intraocular lens device and a direction of the incident light relative to the second intraocular lens device at least partially based on the one or more detection signals;
    with the controller determining a vergence rotation between the first intraocular lens device and the second intraocular lens device based upon a comparison of the direction of the incident light relative to the first intraocular lens device and the direction of the incident light relative to the second intraocular lens device; and with the controller, controllably changing the modifiable focal length of the intraocular lens of at least one of the first intraocular lens device or the second intraocular lens device responsive to the determined vergence rotation between the first intraocular lens device and the second intraocular lens.

2. The method of claim 1, further comprising emitting a light from a light source to produce the incident light.

3. The method of claim 2, wherein emitting the light from the light source includes emitting the light from the light source positioned at or near the intraocular lens device.

4. The method of claim 1, further comprising reflecting the light towards the one or more eyes using at least one light reflector.

5. The method of claim 1, further comprising redirecting the incident light towards the one or more photodetectors using at least one optical element.

6. The method of claim 1, wherein determining the direction of the incident light relative the first intraocular lens device or second intraocular lens device includes determining an angular direction of the incident light source relative the at least one of the first intraocular lens device or second intraocular lens device at least partially based on the one or more detection signals.

7. The method of claim 1, wherein detecting the incident light includes detecting the incident light received at a selected angular direction or an angular range.

8. The method of claim 1, wherein outputting one or more detection signals responsive to the detecting includes outputting the one or more detection signals detected at the first intraocular lens device or at the second intraocular lens device to electrical circuitry of the controller, wherein the electrical circuitry of the controller is located remote from the intraocular lens device.

9. The method of claim 8, further comprising receiving the one or more detection signals, detected at the first intraocular lens device or at the second intraocular lens device, at the electrical circuitry of the controller.

10. The method of claim 1, wherein controllably changing the modifiable focal length of the intraocular lens of at least one of the first intraocular lens device or the second intraocular lens device responsive to the one or more detection signals includes controllably changing the modifiable focal length between two focal lengths.

11. The method of claim 1, wherein controllably changing the modifiable focal length of the intraocular lens of at least one of the first intraocular lens device or the second intraocular lens device responsive to the one or more detection signals includes controllably changing the modifiable focal length between three or more focal lengths.

* * * * *

UNITED STATES PATENT AND TRADEMARK OFFICE
CERTIFICATE OF CORRECTION

PATENT NO. : 10,154,897 B2
APPLICATION NO. : 14/807756
DATED : December 18, 2018
INVENTOR(S) : Jesse R. Cheatham et al.

It is certified that error appears in the above-identified patent and that said Letters Patent is hereby corrected as shown below:

On the Title Page

Item (12) Identification of First Named Inventor, please replace "Cheatham et al." with --Cheatham, III et al.-- therefor Item (72) Inventors, first line, please replace "Jesse R. Cheatham, Seattle, WA (US);" with --Jesse R. Cheatham, III, Seattle, WA (US);-- therefor Item (72) Inventors, fifth line, please replace "Island, WA (US); Lowell L. Wood," with --Island, WA (US); Lowell L. Wood, Jr.,-- therefor Signed and Sealed this
Sixth Day of August, 2019

Andrei Iancu
*Director of the United States Patent and Trademark Office*